US010516262B2

(12) United States Patent
Zmuda

(10) Patent No.: US 10,516,262 B2
(45) Date of Patent: Dec. 24, 2019

(54) OVERVOLTAGE PROTECTION DEVICE AND METHOD

(71) Applicant: Osypka Medical GmbH, Berlin (DE)

(72) Inventor: Paul Zmuda, Gdansk (PL)

(73) Assignee: OSYPKA MEDICAL GMBH, Berlin (DE)

( * ) Notice: Subject to any disclaimer, the term of this patent is extended or adjusted under 35 U.S.C. 154(b) by 455 days.

(21) Appl. No.: 15/366,914

(22) Filed: Dec. 1, 2016

(65) Prior Publication Data

US 2018/0159322 A1   Jun. 7, 2018

(51) Int. Cl.
| H02H 9/04 | (2006.01) |
| H03K 17/081 | (2006.01) |
| A61B 5/0428 | (2006.01) |
| A61N 1/08 | (2006.01) |

(52) U.S. Cl.
CPC ........... *H02H 9/045* (2013.01); *A61B 5/0428* (2013.01); *A61N 1/08* (2013.01); *H03K 17/08104* (2013.01)

(58) Field of Classification Search
CPC .. H02H 9/045; H02H 9/005; H03K 17/08104; A61B 5/0428; A61B 5/04282; A61B 2562/18; A61N 1/08; A61N 1/36125; A61N 1/36142; A61N 1/37; A61N 1/3718; A61N 1/3925
USPC ........................................................ 361/91.2
See application file for complete search history.

(56) References Cited

U.S. PATENT DOCUMENTS

| 4,320,763 | A | | 3/1982 | Money | |
| 4,513,341 | A | * | 4/1985 | Kollanyi | ................ H02H 9/004 361/18 |
| 4,533,970 | A | | 8/1985 | Brown | |
| 4,595,009 | A | | 6/1986 | Leinders | |
| 4,661,979 | A | | 4/1987 | Jakab | |
| 4,744,369 | A | | 5/1988 | Kroll | |
| 4,745,923 | A | | 5/1988 | Winstrom | |
| 4,796,630 | A | | 1/1989 | Regna | |
| 5,517,379 | A | * | 5/1996 | Williams | ............. H02H 11/003 307/127 |
| 5,585,991 | A | * | 12/1996 | Williams | ................ H02H 9/042 361/101 |
| 5,751,531 | A | | 5/1998 | Rault | |
| 5,833,710 | A | * | 11/1998 | Jacobson | ............. A61N 1/3704 607/4 |

(Continued)

FOREIGN PATENT DOCUMENTS

EP   2135639 B1   6/2011

*Primary Examiner* — Zeev V Kitov
(74) *Attorney, Agent, or Firm* — Procopio Cory Hargreaves and Savitch LLP

(57) ABSTRACT

An overvoltage protection device protects an electronic medical device in the event of a transient overvoltage on one or more patient lines of the device. A current limiting device is placed in series in a patient line between electronic components of the medical device and a patient interface. A biasing voltage generating device has at least one biasing element located in a line extending off the patient line and at least one additional circuit element connected in series with the biasing element. The biasing voltage generating device is configured to apply a predetermined biasing voltage to the current limiting device via the biasing element in response to a transient overvoltage on the patient line, whereby the current limiting device is switched off and limits current flow through the patient line.

20 Claims, 24 Drawing Sheets

(56) References Cited

U.S. PATENT DOCUMENTS

| | | | |
|---|---|---|---|
| 8,452,399 B2 | 5/2013 | Wanasek | |
| 8,861,164 B2 * | 10/2014 | Mikolajczak | H02H 3/20 |
| | | | 361/103 |
| 9,026,225 B2 | 5/2015 | Gromotka et al. | |
| 2008/0174184 A1 * | 7/2008 | Arpilliere | H02M 1/08 |
| | | | 307/125 |
| 2013/0253352 A1 * | 9/2013 | Bornzin | A61N 1/37 |
| | | | 600/509 |
| 2016/0276827 A1 * | 9/2016 | Coyne | H02H 9/041 |

* cited by examiner

OVERVOLTAGE PROTECTION DEVICE AND METHOD

BACKGROUND

Related Field

The subject matter discussed herein relates generally to overvoltage protection devices or circuits and methods, and particularly to overvoltage protection devices and methods for electrical or electronic medical devices.

Related Background

Active electrical devices intended for medical and veterinary applications usually serve specific purpose. ECG monitors are used to obtain an electrocardiogram, hemodynamic monitors employing measurement of electrical impedance apply an electrical auxiliary current, electrocautery knifes and other electrosurgical devices are used in the operating room, electrical pulse generators emit electrical stimuli for stimulation of cardiac tissue or nerves, and cardiac defibrillators apply high voltage pulses towards the heart to overcome fibrillation. The chance that more than one such device is used on the same patient at the same time is high. It is therefore important to shield each electrical or electronic medical device from damage resulting from the electrical energy applied by another such device ("protection requirement"). Electrical medical devices should also be designed not to absorb the energy applied by another device for treatment of the patient or animal ("energy reduction requirement").

The compatibility between electrical devices applied simultaneously to a patient or animal is of particular of importance upon applying a defibrillation pulse to the patient. Defibrillation pulses with voltage amplitude reaching or exceeding several hundreds and even thousands of volts ("overvoltage") create a challenge for other electrical medical devices used at the same time. The challenge is greater for devices emitting electrical pulses (pacemakers) or signal waveforms (patient auxiliary currents). Such devices have a low impedance interface towards the patient (or animal). For instance, the two states in which a pacemaker usually exhibits low impedance of the patient line interfaces is during the stimulation pulse and the discharge period immediately following the stimulation pulse. While pacemakers require a patient line interface impedance in the range of a few ohms, bio-impedance based monitors typically operate with impedances of several hundreds of ohms up to about 1 kΩ. In summary, any impedance added in the interface for protective reasons might compromise the function of the emitting device.

A simple protection against defibrillation pulses can be achieved by employing a transient voltage suppressor diode (TVS) in conjunction with a "protection resistor" in series with the patient (human or animal) line interface, and applied to each patient line interface. In order to achieve a suitable defibrillation energy reduction, the value of a defibrillation protection resistor cannot be small. Instead, a relative high-ohmic resistor is required. Thus, this simple defibrillation protection approach cannot be used in active electrical devices such as cardiac pacemakers and biompedance-based monitors which require a low impedance interface.

A commonly used approach to switch between a low impedance patient interface during normal operation and a high impedance interface upon occurrence of overvoltage is the employment of depletion mode metal-oxide-semiconductor field-effect transistors (MOSFETs) in line with the patient interface. These devices act as current limiters, since a MOSFET in off-state allows only minimal current passing through.

Many known overvoltage protection circuits for medical devices have in common an element in series with the patient line interface to bias a MOSFET transistor so that it can impede current sufficiently. This element may comprise a resistor or another transistor. In either case, this element increases the impedance of the patient line interface during normal operation by a smaller amount employing a transistor and by a larger amount using a resistor. In addition to this drawback, some solutions employ a relatively complicated MOSFET biasing technique, which is dependent on biasing voltages generated by the protected device itself. This may lead to compromising situations because the protection is relying on an internal voltage, the level of which can become questionable due to a fault or battery exhaustion.

Some protection circuits have capacitors in series with each patient line interface. The capacitors change the shape of incoming transients in such a way that only a fraction of the initial overvoltage transient energy is passing through. The remaining voltage is clamped by voltage limiting devices such as Zener diodes. The combination of a capacitor and a Zener-diode repels the incoming energy. A potential shortcoming of such a circuit is related to the capacitors. A reliable protection against high voltage transients requires the use of special high voltage capacitors which are not of the ordinary type and, accordingly, most likely expensive and/or hard to get. Another potential shortcoming is that the sensitivity of the protection circuit is dependent on the value of applied capacitors. Such protection circuits may be trimmed in view of the expected overvoltage transients, which is not a desired property of an overvoltage protection circuit. Moreover, the required capacitors connected in series with each patient interface line establish an impedance, the value of which, unfortunately, is also dependent on the capacitor value.

SUMMARY

In one aspect, an overvoltage protection circuit between a patient interface and an electrical medical device employs current limiter devices such as depletion mode metal-oxide-semiconductor field-effect transistors (MOSFETs) placed in the patient current path or line in combination with a circuit arranged for generating a bias voltage to turn off an associated MOSFET in the event of a transient voltage pulse. In one aspect, the bias voltage is obtained from a biasing resistor connected at one end to the patient current path or patient interface line, and extending off the patient line in series with a transient voltage suppressor (TVS). The TVS may be a unidirectional or a bidirectional TVS or a second resistor in series with the biasing resistor to form a voltage divider. With this arrangement, the protective components are not placed directly in the patient line connected between operative electronic components of the medical device and a patient interface.

In another aspect, a medical device is provided which comprises one or more electronic components, at least one patient channel having first and second patient lines for connecting electrical signals to and/or from the electronic components of the medical device, patient interfaces connected to the patient channel, and an overvoltage protection device or circuit associated with the patient channel and comprising a first current limiter device located in the first patient line or current path, a second current limiter device located in the second patient line, and first and second bias voltage generating devices located outside the first and second patient lines, respectively, and configured to generate a predetermined biasing voltage to turn off the respective first or second current limiting device to limit current flow through the first or second line, respectively, in response to a transient overvoltage on the first or second line.

In one aspect, the first and second voltage generating devices comprise respective first and second biasing resistors each connected at one end to the respective first or second patient line, and at least one voltage limiting device or transient voltage suppressor connected in series between the respective first and second biasing resistors. In one embodiment, the voltage limiting device comprises one bidirectional voltage limiting device connected between the second ends of the biasing resistors. In another embodiment, a first unidirectional voltage limiting device is connected to the first biasing resistor and a second unidirectional voltage limiting device is connected to the second biasing resistor, and the first and second unidirectional voltage limiting devices are tied together. In another embodiment, the first and second biasing resistors are each connected in series with a respective additional resistor to form a first and second voltage divider, with the junction between the resistors of the first voltage divider connected to the first current limiter device and the junction between the resistors of the second voltage divider connected to the second current limiter device.

In one embodiment, a biasing resistor is connected in series with a transient voltage suppressor diode (TVS) and is also connected between the MOSFET source and gate terminals. Upon an occurrence of an overvoltage, which has the shape of a steep ramp, initially a small current flows through the resistor. Once the voltage across this resistor reaches the required bias level of the MOSFET, the MOSFET shuts off the patient interface line and, as a result, the current flows through the resistor. The voltage limiting capability of the TVS is only required at the very beginning of the transient overvoltage just to cause a small current flow through the resistor connected in series with the TVS. In an alternative embodiment the TVS can be replaced by resistors. In another embodiment, the biasing resistor is connected in series with a second resistor to form a voltage divider, with the junction between the resistors connected to the MOSFET gate terminal.

The overvoltage protection circuit or device is designed to have a very quick response to the transient overvoltage. The MOSFETs are in the off-state almost at the onset of the overvoltage ramp, before the overvoltage has reached its peak. Also, the bias circuitry does not require an additional impedance element in the patient line interface.

In one aspect, the overvoltage protection circuit adds only one component to patient interface line, specifically a current limiter device such as a MOSFET which is either in an on or off state.

The overvoltage protection circuit may be incorporated in or used in conjunction with any medical devices which output (emit) a voltage/current signal or pulse (such as cardiac and nerve stimulators or bio-impedance based monitors). These devices feature a low resistance interface to a patient (or animal). In case of overvoltage applications, such as defibrillation pulses, these devices are highly susceptible to damage as well as diverting the applied energy intended for the patient, away from the patient. The overvoltage protection circuit is designed to shut off the patient line or lines with which it is associated on occurrence of an excess voltage such as a defibrillation pulse on the line.

BRIEF DESCRIPTION OF THE DRAWINGS

The details of various embodiments can be gleaned in part from a study of the accompanying drawings, in which like reference numbers refer to like parts, and in which.

DETAILED DESCRIPTION

Certain embodiments as disclosed herein provide for an overvoltage protection system or circuit designed to generate a bias voltage via circuit components which are not located directly in series with one or more patient line interfaces connected to outputs or inputs of an electrical medical device for treatment or monitoring purposes, such as implantable or external devices including ECG monitors, hemodynamic monitors, electrocautery knives or other electrical surgical devices, electrical pulse generators or pacemakers for cardiac stimulation or nerve stimulation, and cardiac defibrillators and the like.

The subject matter described herein is taught by way of example implementations. Various details have been omitted for the sake of clarity and to avoid obscuring the subject matter. The examples shown below are directed to overvoltage protection devices, systems and methods for electronic medical devices. Features and advantages of the subject matter should be apparent from the following description.

After reading this description it will become apparent to one skilled in the art how to implement the invention in various alternative embodiments and alternative applications. However, all the various embodiments of the present invention will not be described herein. It is understood that the embodiments presented here are presented by way of an example only, and not limitation.

Figure 1:
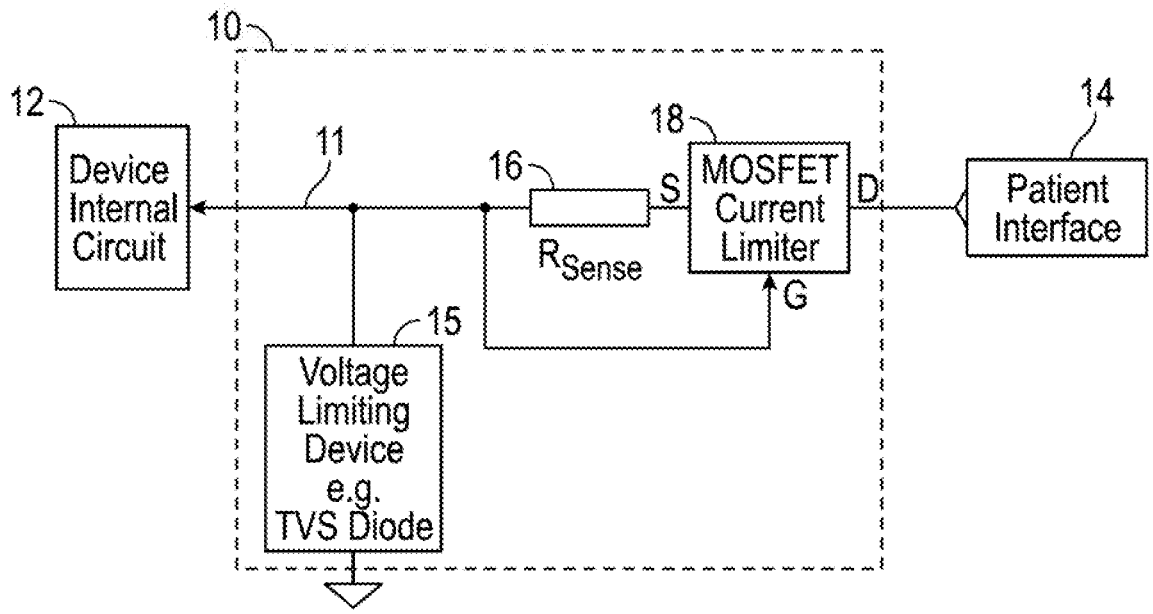
FIG. 1 is a block diagram illustrating a prior art overvoltage protection circuit of a medical device.

FIG. 1 illustrates a conventional prior art circuit or overvoltage protection device 10 connected in series in the patient line 11 between an electronic medical device 12 and a patient interface 14. The device 10 provides protection against overvoltage by means of a transient voltage suppressor diode (TVS) 15 connected between the patient line 11 and ground, and a protection resistor (impedance) 16 and a MOSFET current limiter 18 which are connected in patient line 11 in series with the patient line interface 14. In this arrangement, if an overvoltage pulse occurs, the MOSFET is turned off. In order to achieve a suitable defibrillation energy reduction, the ohmic value of the defibrillation or overvoltage protection resistor 16 cannot be small. Instead, a relatively high-ohmic resistor is required. Thus, this simple defibrillation protection approach cannot be used in active electrical devices such as cardiac pacemakers and biompedance-based monitors which require a low impedance interface.

Figure 2:
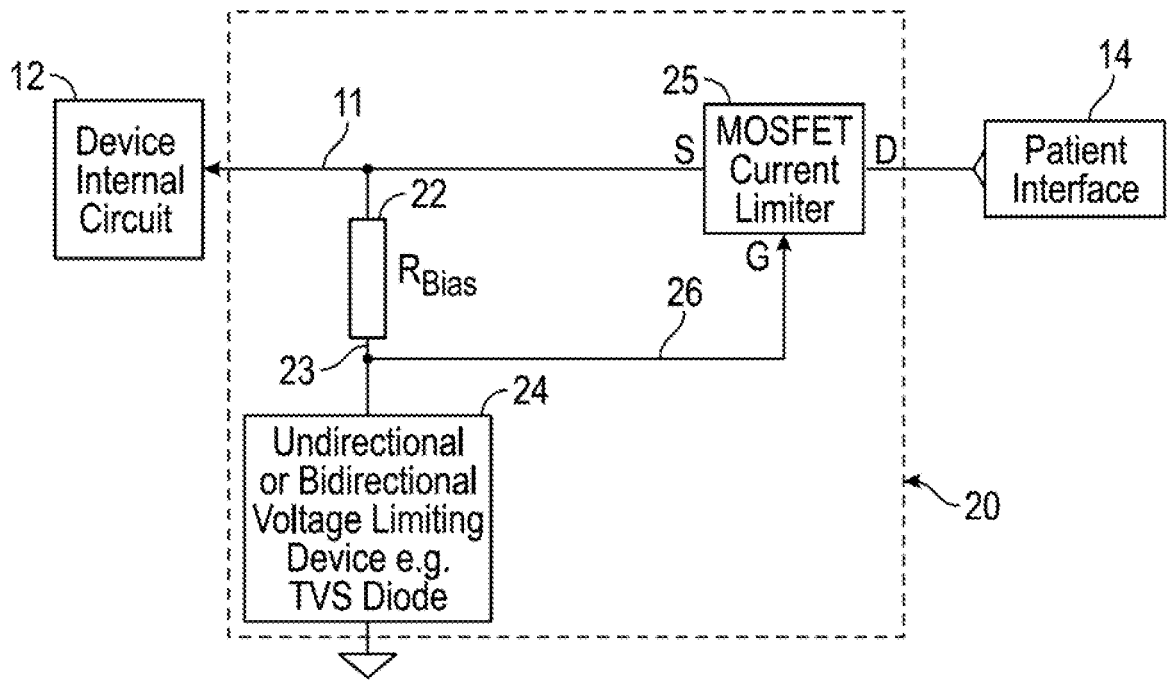
FIG. 2 illustrates one embodiment of an overvoltage protection system or circuit for an electrical or electronic medical device connected to one patient line interface.

FIG. 2 illustrates a first embodiment of an overvoltage protection device or circuit 20 which has no resistor or impedance directly in the patient line 11 in series with patient line interface 14 and medical device internal circuit 12. The embodiment of FIG. 2 is illustrated with one patient line interface 11, but modified embodiments are provided to provide overvoltage protection for two patient interfaces (one patient channel), or for two, three or more patient channels, depending on the number of channels provided in the medical device. The overvoltage protection circuits described below may be incorporated in an electronic medical device itself between electronic components and patient interfaces, or may be separate devices for incorporation between the medical device and patient.

In one embodiment, the overvoltage protection circuit employs current limiter devices such as depletion mode MOSFETs in the patient lines or current paths, in combination with biasing voltage generating devices which are not located in any patient line or patient current path, and which are configured to establish the bias voltage for the current limiting devices in the event of a overvoltage. FIG. 2 shows one embodiment of an overvoltage protection circuit associated with one patient line, to illustrate the operation principle. In this configuration, the patient line is protected only in one direction. In some variations, each patient channel is equipped with the overvoltage protection circuit 20 to provide protection which is independent of the direction of the applied transient voltage, as described in more detail below in connection with FIGS. 3 to 12.

In FIG. 2, a current limiter 25 such as a MOSFET or the like is placed in the current path or first line 11 between patient interface 14 and the internal circuit 12 of an electrical or electronic medical device. A biasing voltage generating circuit or device is placed in a second line 23 extending off patient 11 and comprises a biasing resistor 22 connected at one end to the patient current path or line 11 at a location between MOSFET 25 and the medical device internal circuit, and in series with a transient voltage limiting device such as a TVS diode 24 on line 23. The junction between biasing resistor 22 and TVS diode 24 is connected via line 26 to the MOSFET gate terminal G.

In this approach, the bias voltage for the MOSFET is obtained from a resistor placed outside the MOSFET current path (and thus outside the patient current path, or patient interface line), and in particular, placed in series with a transient voltage suppressor (TVS), which can either be a unidirectional or a bidirectional TVS. This avoids having a resistive element connected in series on line 11 between the MOSFET and the device internal circuit 12, unlike the prior art arrangement of FIG. 1.

In some embodiments, the biasing resistor has a resistance selected to produce a sufficient bias voltage to turn off the MOSFET relatively quickly in the event of an overvoltage transient. In some embodiments, a resistor having a resistance of 100Ω is connected in series with transient voltage suppressor diode (TVS) 24, but biasing resistors having different resistance values may be used in some embodiments, for example with resistance in the range of 50 ohms to 1 kOhm. The resistor 22 placed outside the MOSFET current path together with TVS diode 24 is used to generate a bias voltage for the depletion mode MOSFET 25. This bias voltage is then applied via lines 11 and 26 between the source and gate terminals S, G of the MOSFET current limiter to turn it off if a transient overvoltage occurs at the input of the patient interface. The depletion mode MOSFET exhibits high impedance at the very beginning of a transient voltage pulse, since a small current starts to flow through resistor 22 as the TVS starts to conduct. A TVS diode is selected which conducts at a fraction of the voltage of a typical transient overvoltage. In many devices such as pacemakers or hemodynamic monitors, the applied TVS starts breakdown for voltages of 20 V . . . 24 V. With a biasing resistor of 100Ω, testing has shown that about 30 mA of current through biasing resistor 22 turns off the MOSFET. Such a current flows almost instantly after the TVS diode starts to conduct (breaks down), providing a faster response to transient overvoltages.

Figure 3:
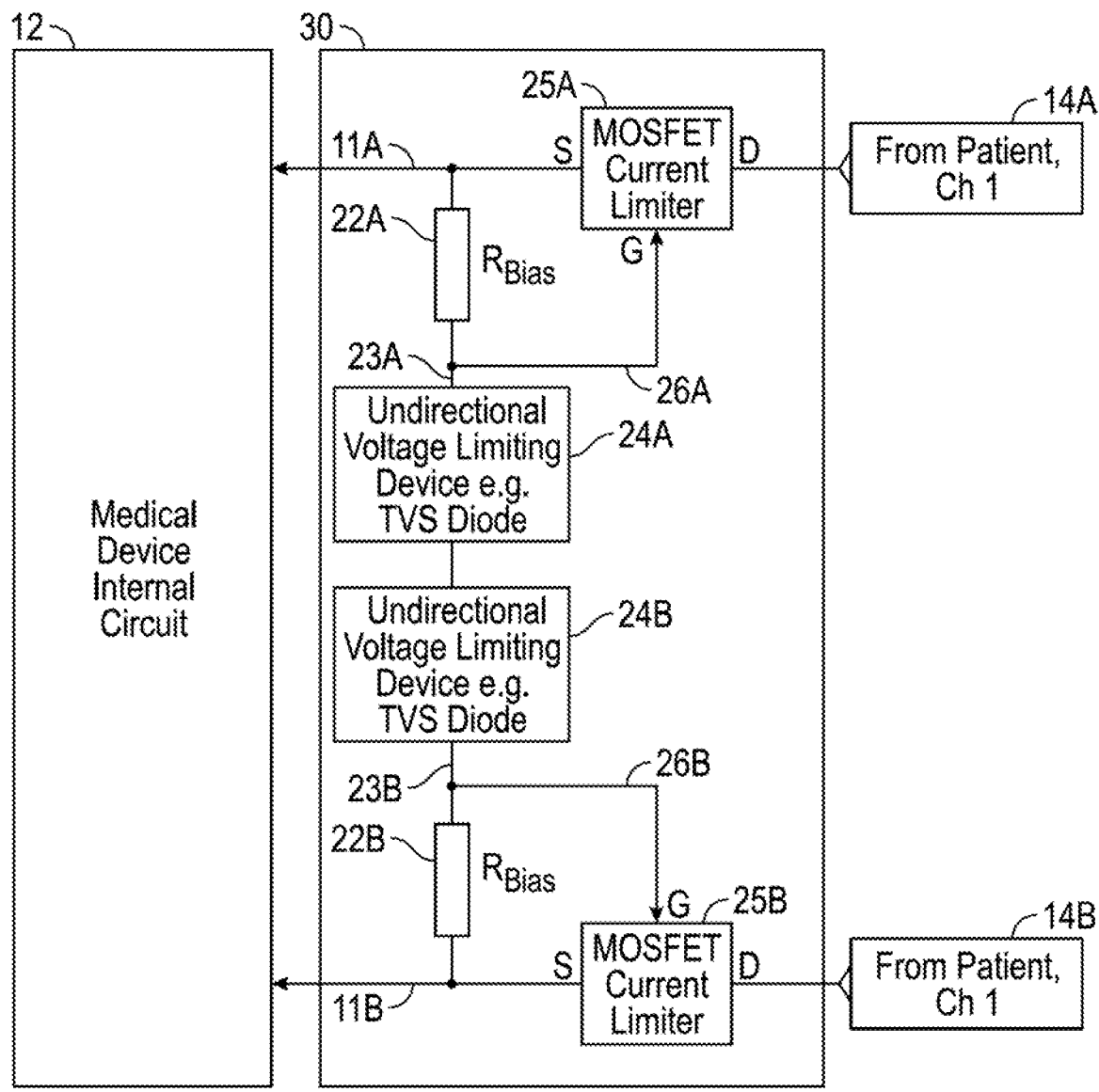
FIG. 3 illustrates a modification of the system of FIG. 2 for connection to two patient line interfaces of a patient channel.

FIG. 3 illustrates a modified embodiment of an overvoltage protection device or circuit 30 for two patient lines 11A, 11B forming a patient channel of an electrical medical device and having patient interfaces 14A and 14B. Circuit 30 uses similar or identical components to the circuit 20 of FIG. 2. A first biasing resistor 22A has a first end connected to patient line 11A and is connected in series with first unidirectional transient voltage suppressor (TVS) 24A on line 23A extending off the patient line and is also connected via line 26B extending from a junction between first biasing resistor 22A and first unidirectional TVS 24A to the gate of MOSFET 25A. A second biasing resistor 22B has a first end connected to patient line 11B and is connected in series with second unidirectional TVS 24B via line 23B extending off the patient line and connected via line 26B extending from a junction between biasing resistor 22B and unidirectional TVS 24B to the gate of MOSFET 25B located in patient line 11B. The unidirectional TVS diodes 24A and 24B are tied together at their adjacent ends either with their cathodes or anodes. The protection circuit is connected to a patient channel of an electronic medical device, for example a single chamber pacemaker or one channel of a hemodynamic monitor, or other types of medical devices. The circuit 30 is designed to provide overvoltage protection to the two line patient channel upon and during occurrence of overvoltage of each polarity, in order to avoid or reduce the risk of the internal circuit 12 of the medical device absorbing the energy contained in the overvoltage.

Figure 4:
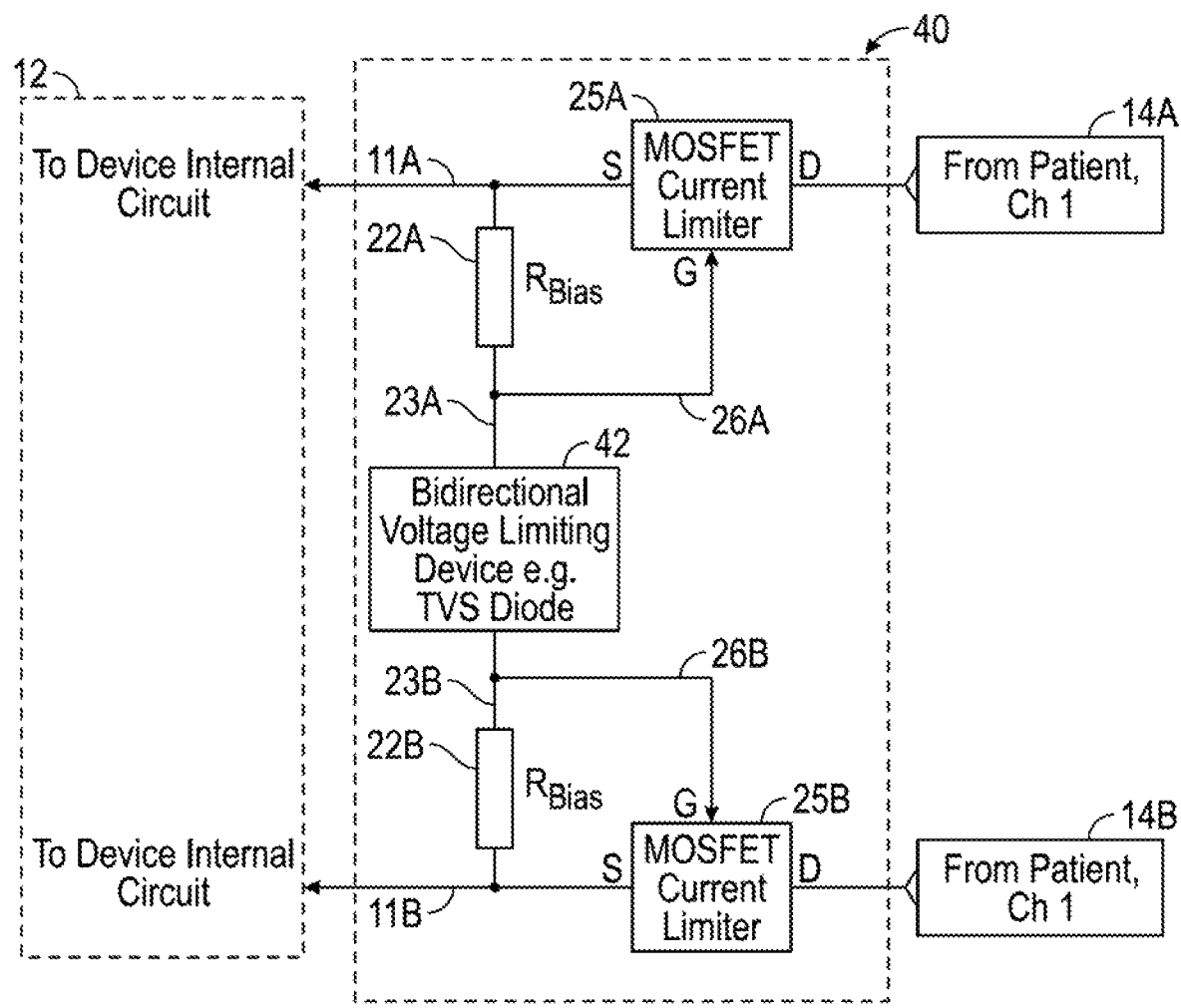
FIG. 4 illustrates a modification of the system or circuit of FIG. 3 in which the unidirectional voltage limiting devices are replaced with a single, bidirectional voltage limiting device.

FIG. 4 illustrates a modified overvoltage protection circuit 40 which is similar to circuit 30 of FIG. 3 but replaces unidirectional voltage limiting devices 24A, 24B with a single, bidirectional voltage limiting device such as a bi-directional TVS diode 42. Other parts of the circuit or device 40 are the same as components of the circuit 30 of FIG. 3, and like reference numbers are used for like parts as appropriate. The bidirectional TVS can be mounted in either direction. As in FIG. 3, the circuit is applied to a patient channel consisting of two patient lines, which may be a single chamber pacemaker or one channel of a hemodynamic monitor, or the like.

Figure 5A:
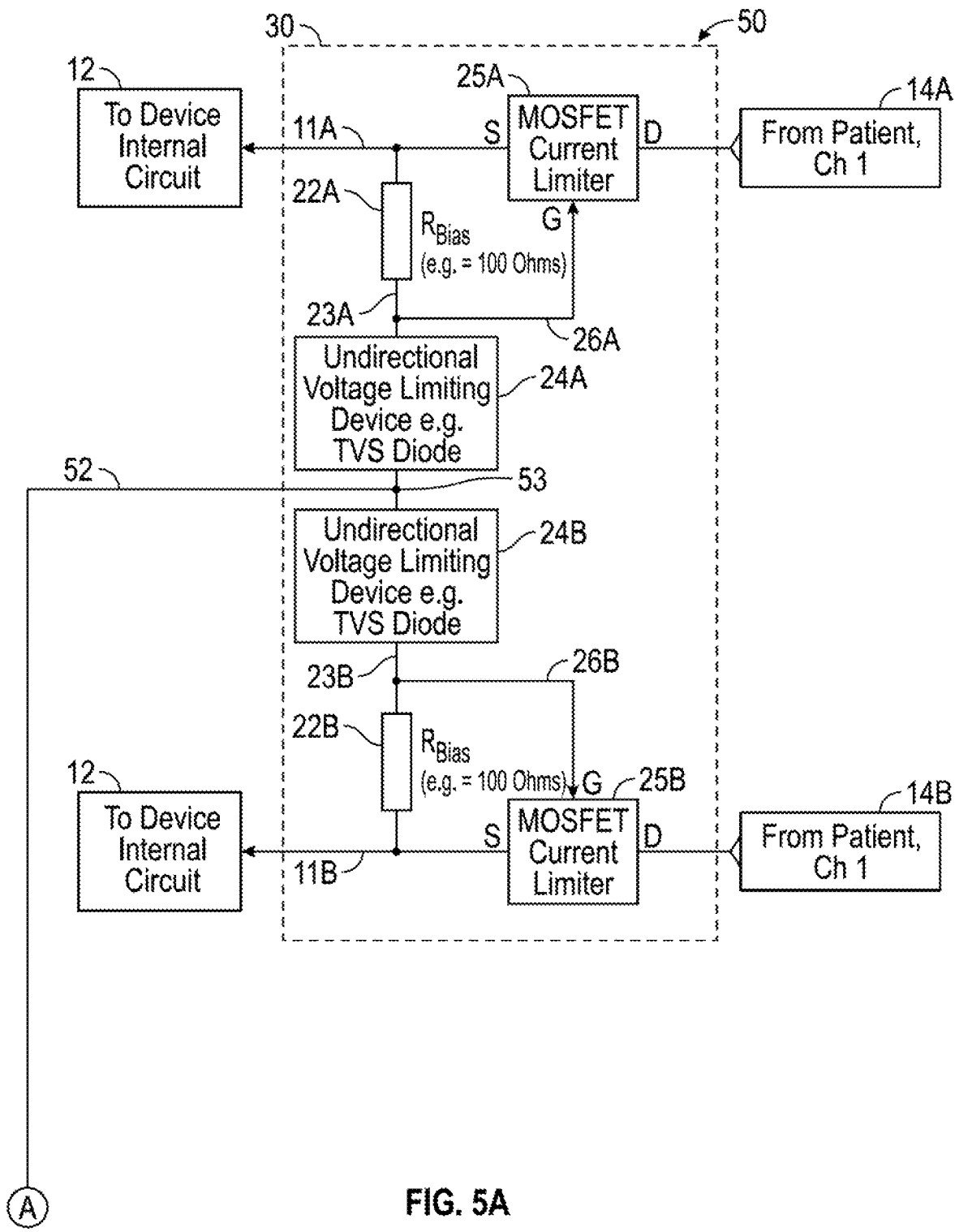
FIGS. 5A and 5B illustrate a modified overvoltage protection system for four patient line interfaces of two channels of a medical device.
Figure 5B:
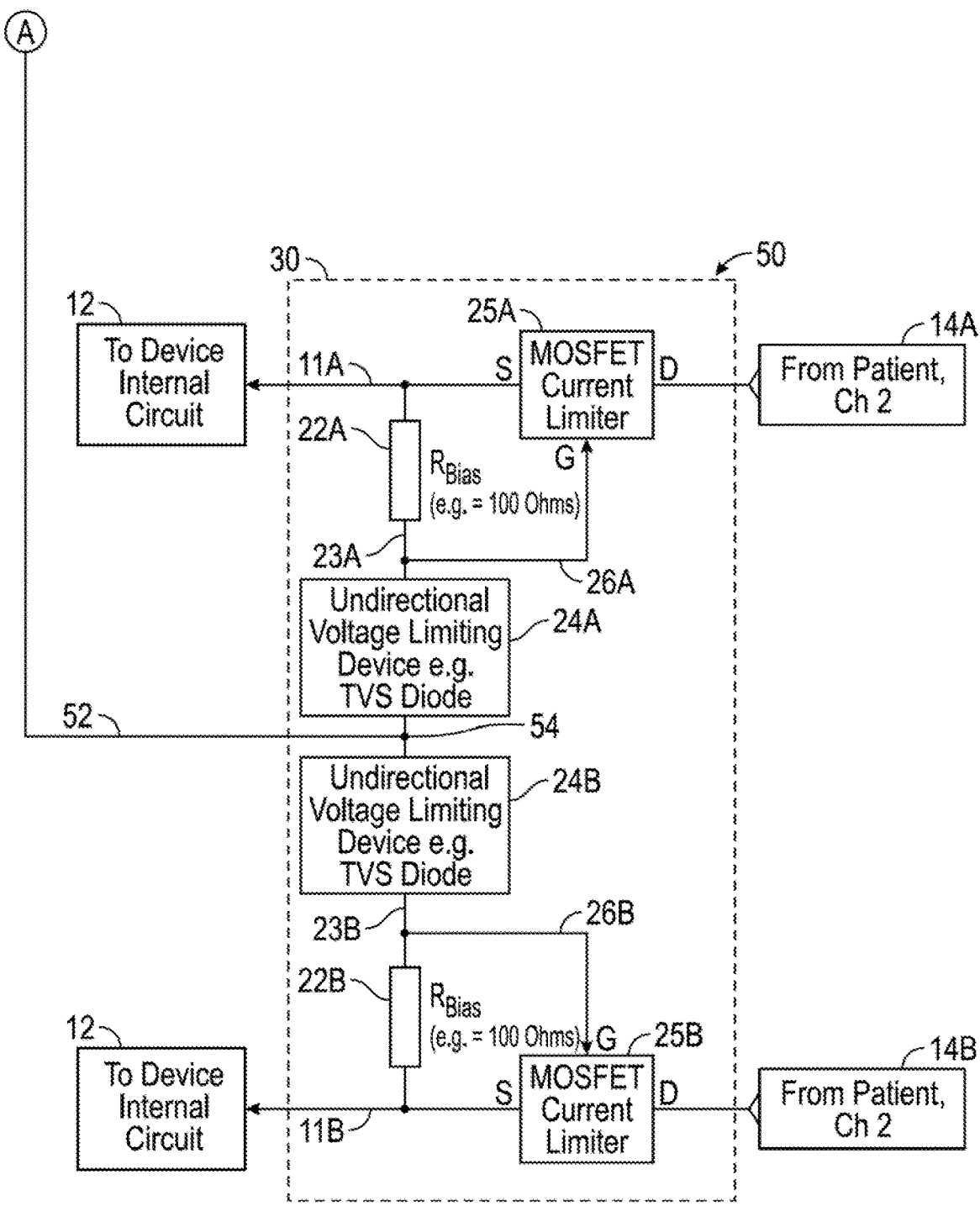

FIGS. 5A and 5B illustrate one embodiment of a modified overvoltage protection circuit or device 50 which is configured to provide overvoltage pulse protection for an electronic medical device having two patient channels, such as a dual-chamber pacemaker, or two channels of a hemodynamic monitor. Device 50 comprises two of the single channel circuits 30 of FIG. 3 applied to the respective channels of a dual channel device, and like reference numbers are used for like parts as appropriate. As in FIG. 3, the circuit 30 of each channel has a first biasing resistor 22A connected at one end to patient line 11A and connected in series with first unidirectional transient voltage suppressor (TVS) 24A on line 23A, and connected via line 26A extending from a junction between resistor 22A and TVS 24A to the gate of MOSFET 25A, and a second biasing resistor 22B connected at one end to patient line 11B and connected in series with second unidirectional TVS 24B via line 23B, and connected to the gate of MOSFET 25B via line 26B. As in FIG. 3, the unidirectional TVS devices are tied together at their ends either with their cathodes or anodes. The two circuits are linked via line 52 extending between nodes 53 (FIG. 5A) and 54 (FIG. 5B) located between TVS 24A and 24B in the respective circuits.

An example of where this circuit can be used is a dual chamber pacemaker or two channels of a hemodynamic monitor. Circuit 50 provides overvoltage protection for two channels, i.e. it protects the device upon and during occurrence of the overvoltage of each polarity between any patient lines and avoids or reduces the risk of the device absorbing the energy contained in the overvoltage.

Figure 6A:
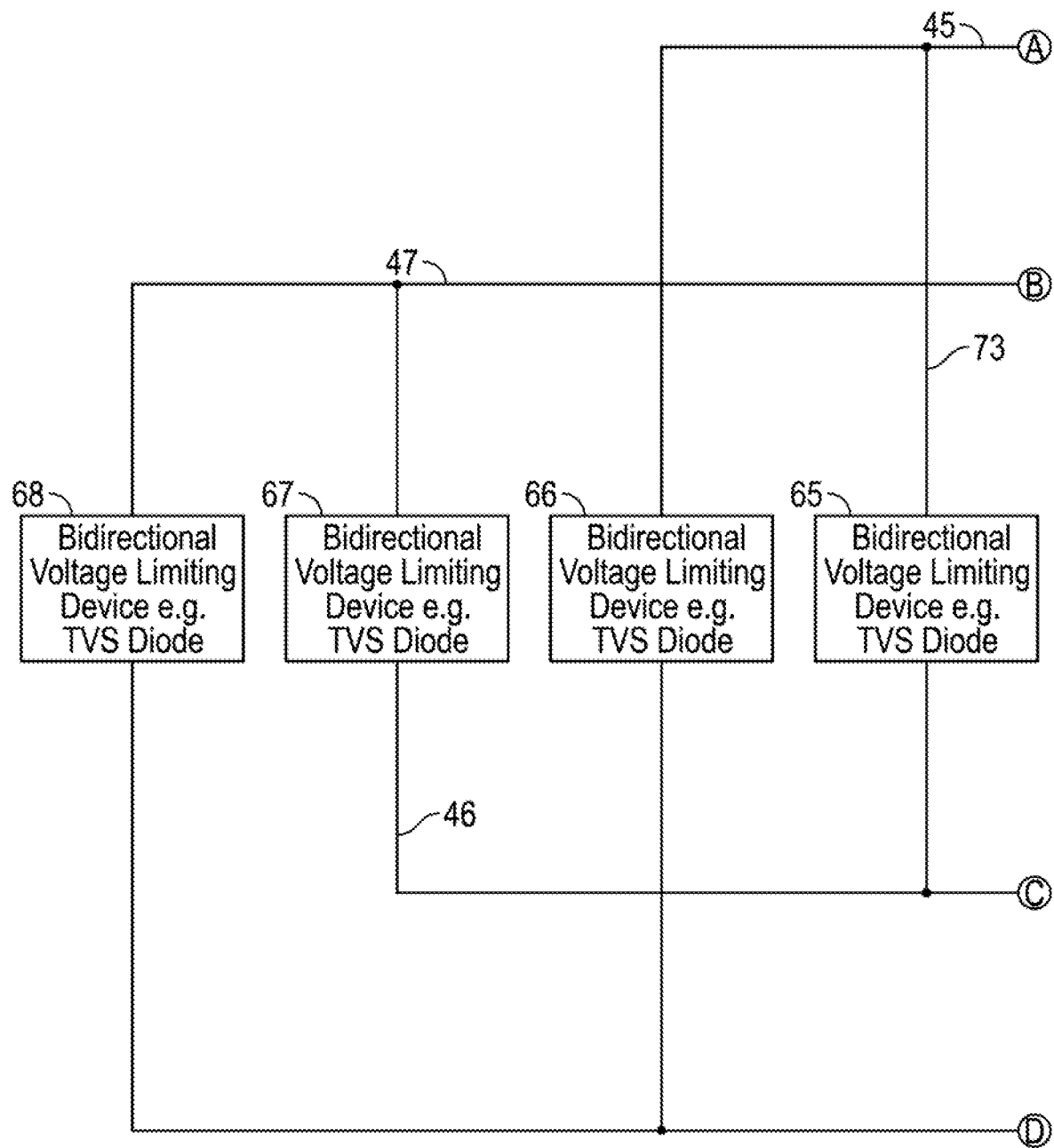
FIGS. 6A and 6B illustrate an embodiment of an overvoltage protection system or circuit designed for four patient line interfaces of an electrical medical device.
Figure 6B:
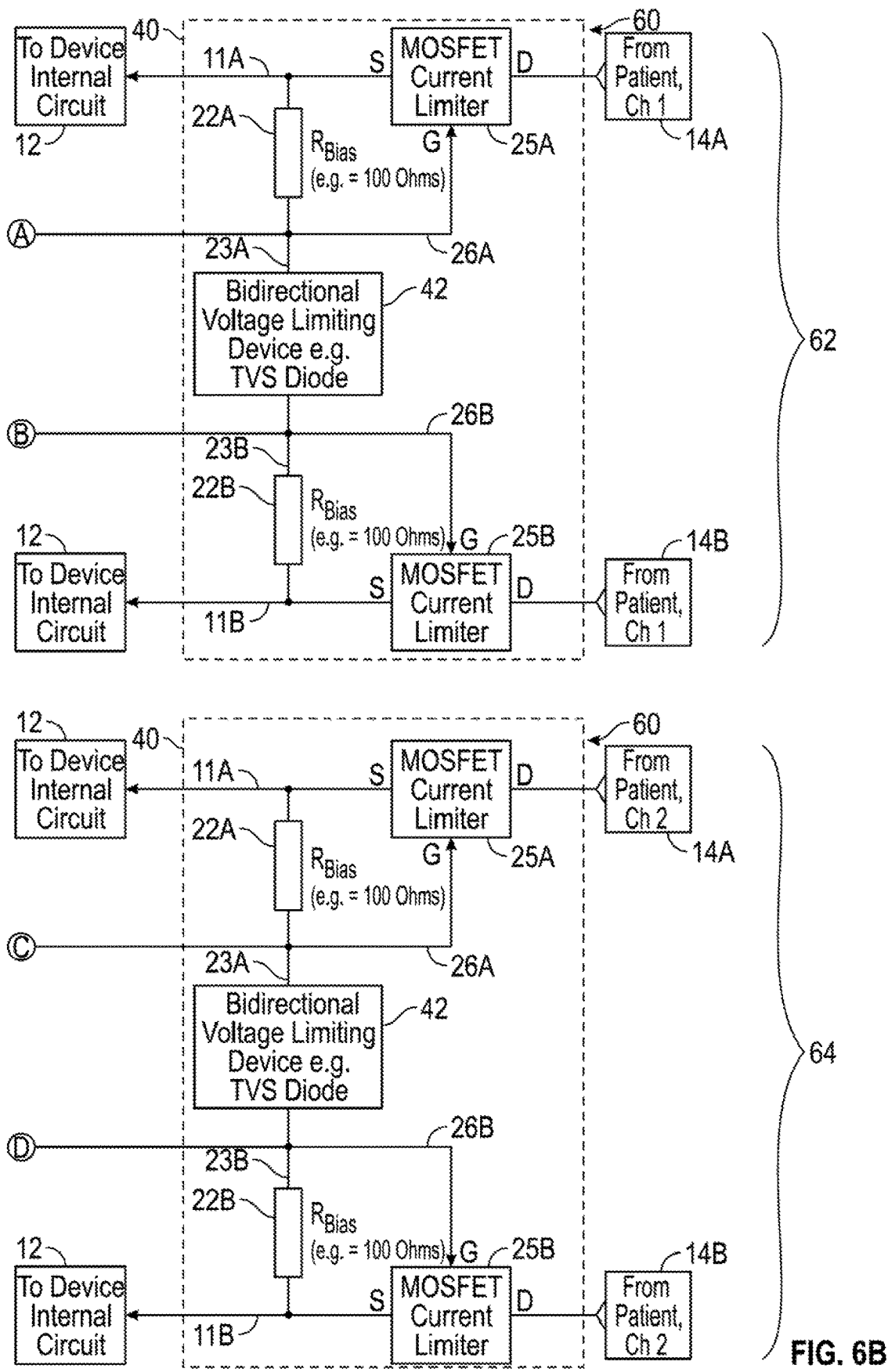

FIGS. 6A and 6B illustrate an embodiment of an overvoltage protection circuit 60 similar to that of FIG. 4 but modified for protecting a two channel patient interface, by generating a bias voltage using a respective resistor (impedance) connected to the patient line interface for each of the four patient line interfaces applicable, for instance, for the two patient channels of a dual-chamber pacemaker or two channels of a hemodynamic monitor. This is similar to the previous embodiment of FIGS. 5A and 5B but employs a single bidirectional TVS diode 42 in each channel 62, 64 between biasing resistors 22A and 22B rather than two unidirectional TVS diodes 24A, 24B as in FIGS. 3 and 5A, 5B.

In this embodiment, four additional bidirectional voltage limiting devices or TVS diodes 65, 66, 67 and 68 (seen in FIG. 6A) are connected in lines between biasing resistors in the two patient channels 62, 64 (seen in FIG. 6B) to activate the current limiting capability of circuit 60 in the event that a transient voltage occurs across patient lines belonging to two different channels. As illustrated in FIG. 6B, a first bidirectional TVS device 65 is located in line 73 between the second ends of resistors 22A in the first and second patient channels, TVS device 66 is located in line 45 connected between the second end of resistor 22A in the first patient channel 62 and the second end of resistor 22B in the second patient channel, TVS device 67 is located in line 46 connected between the second end of resistor 22B in the first patient channel and the second end of resistor 22A in the second patient channel, and TVS device 68 is located in line 47 connected between the second end of resistor 22B in the first patient channel and the second end of resistor 22B in the second patient channel. This protects the medical device against overvoltage of either polarity between any pair of patient lines. Thus, this embodiment requires two more TVS devices than the previous embodiment using unidirectional TVS (see FIG. 5A, 5B).

Figure 7A:
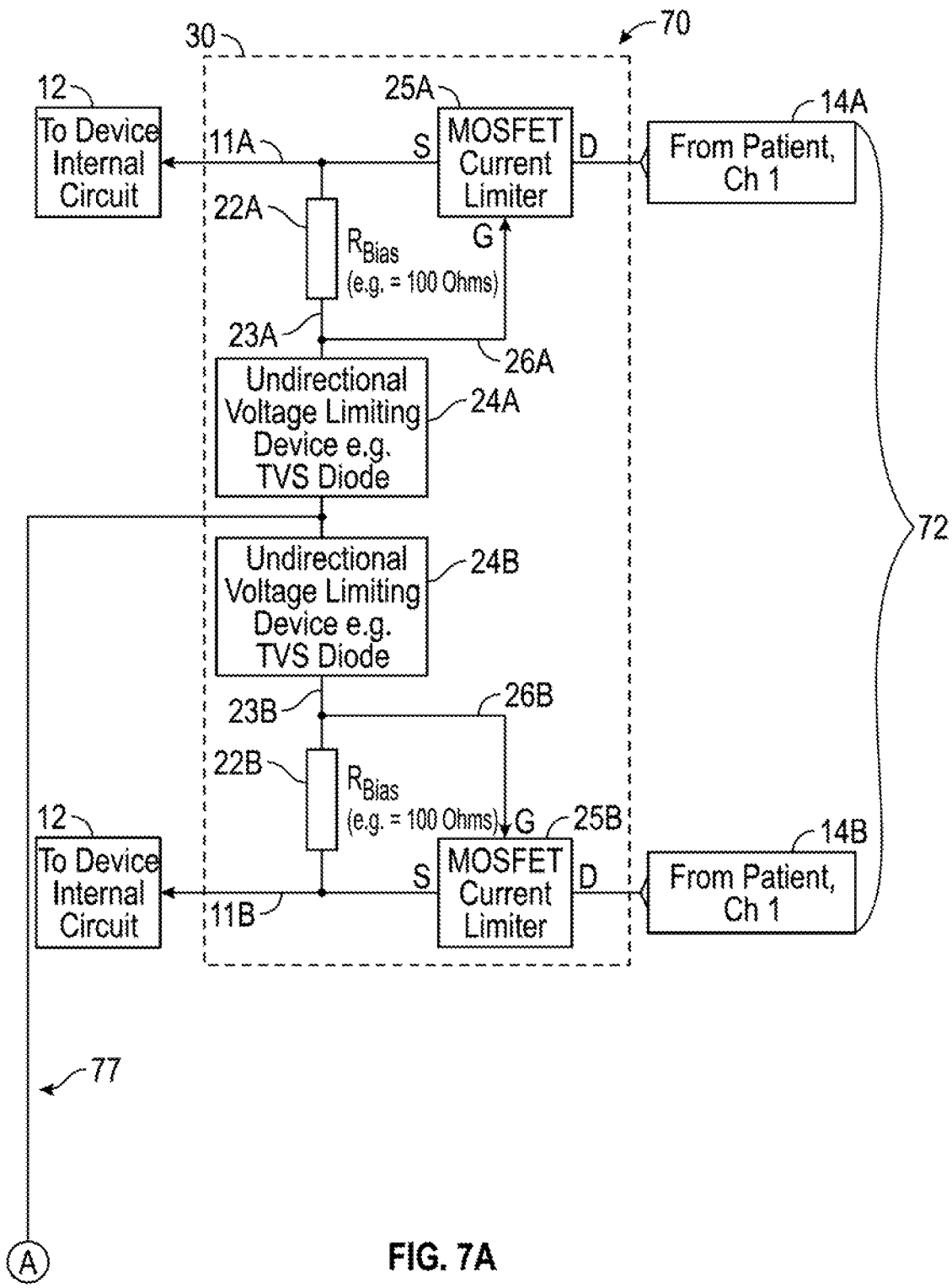
FIGS. 7A, 7B and 7C illustrate another embodiment of an overvoltage protection circuit or system having six patient line interfaces (three channels)
Figure 7B:
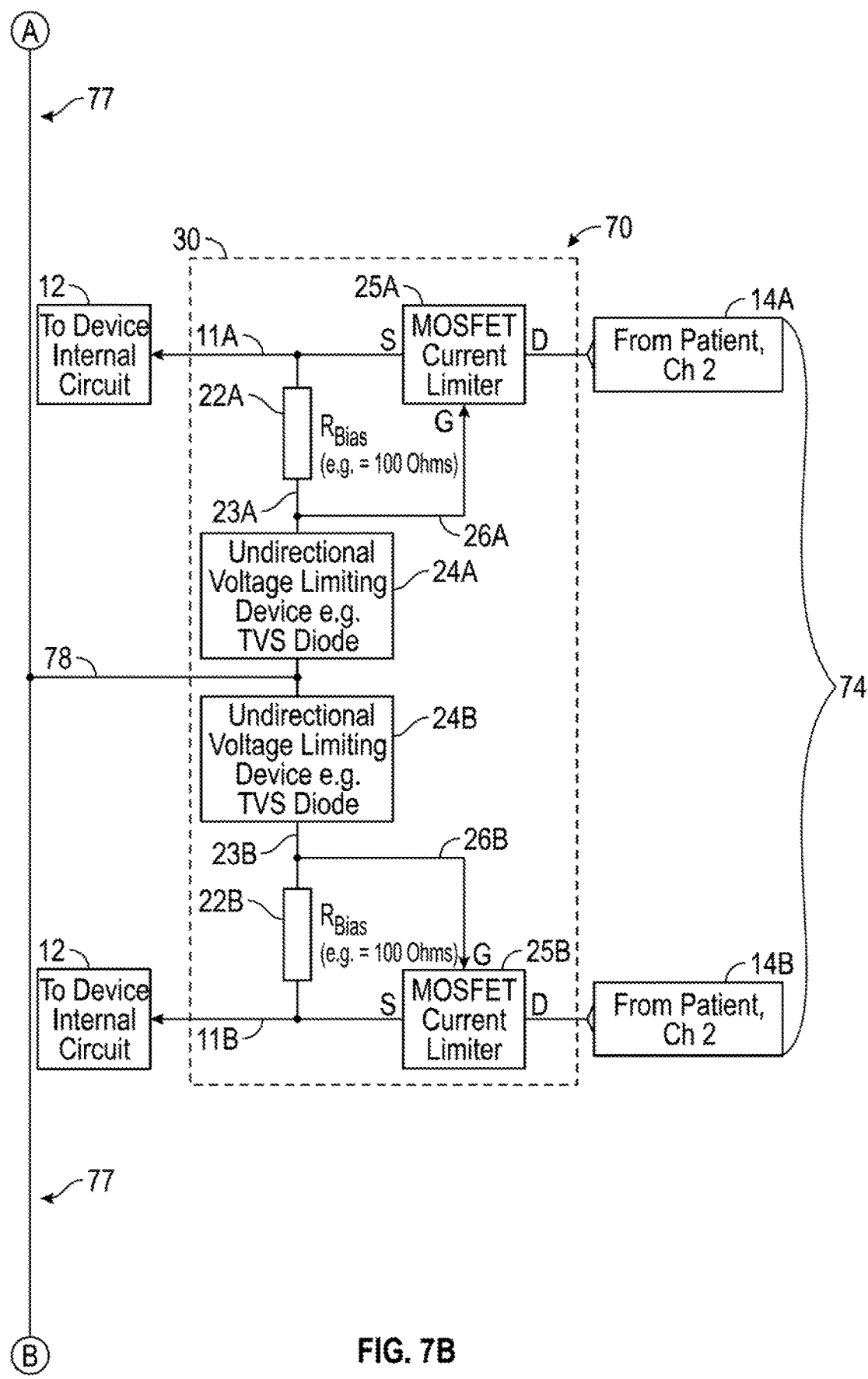
Figure 7C:
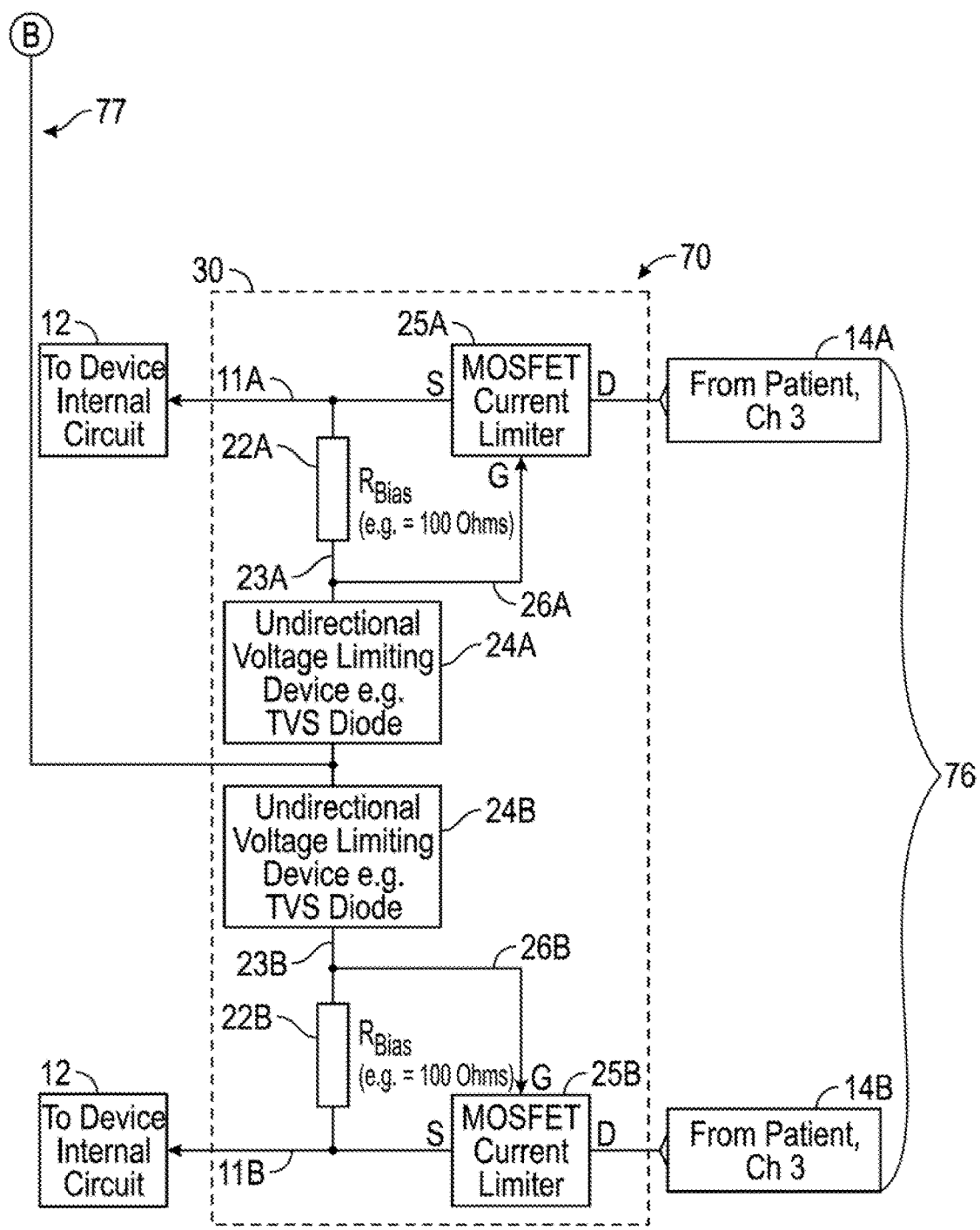

FIGS. 7A to 7C illustrate an embodiment of an overvoltage protection circuit 70 similar to that of FIGS. 5A and 5B but modified for protecting three patient channels, such as the three patient channels of a triple chamber or bi-ventricular pacemaker or a hemodynamic monitor having three patient channels. Circuit 70 of FIGS. 7A to 7C includes three of the overvoltage protection circuits 30 of FIGS. 3, 5A and 5B applied to a three channel patient interface of a medical device having three patient channels 72, 74, 76, rather than two channels as in FIG. 5B, and like reference numbers are used for like parts as appropriate. Circuit 70 is designed for generating a bias voltage using a respective biasing resistor (impedance) 22A or 22B having a first end connected to each patient line interface of the six patient line interfaces in the same manner as described above in connection with FIGS. 5A and 5B. As in FIGS. 5A and 5B, this circuit employs unidirectional TVS.

As in FIGS. 5A, 5B, the respective pairs of unidirectional TVS 24A, 24B are tied together at their ends either with their cathodes or anodes. Junctions between respective TVS pairs in the different channels are connected together via lines 77, 78 as seen in FIGS. 7A to 7C, to provide current limiting capability in case a transient voltage occurs across patient lines belonging to different patient channels. The overvoltage protection circuit 70 provides overvoltage protection for three channels, i.e. it protects the device upon and during occurrence of the overvoltage of each polarity between any patient lines and reduces or eliminates the risk of the device absorbing the energy contained in the overvoltage.

Figure 8A:
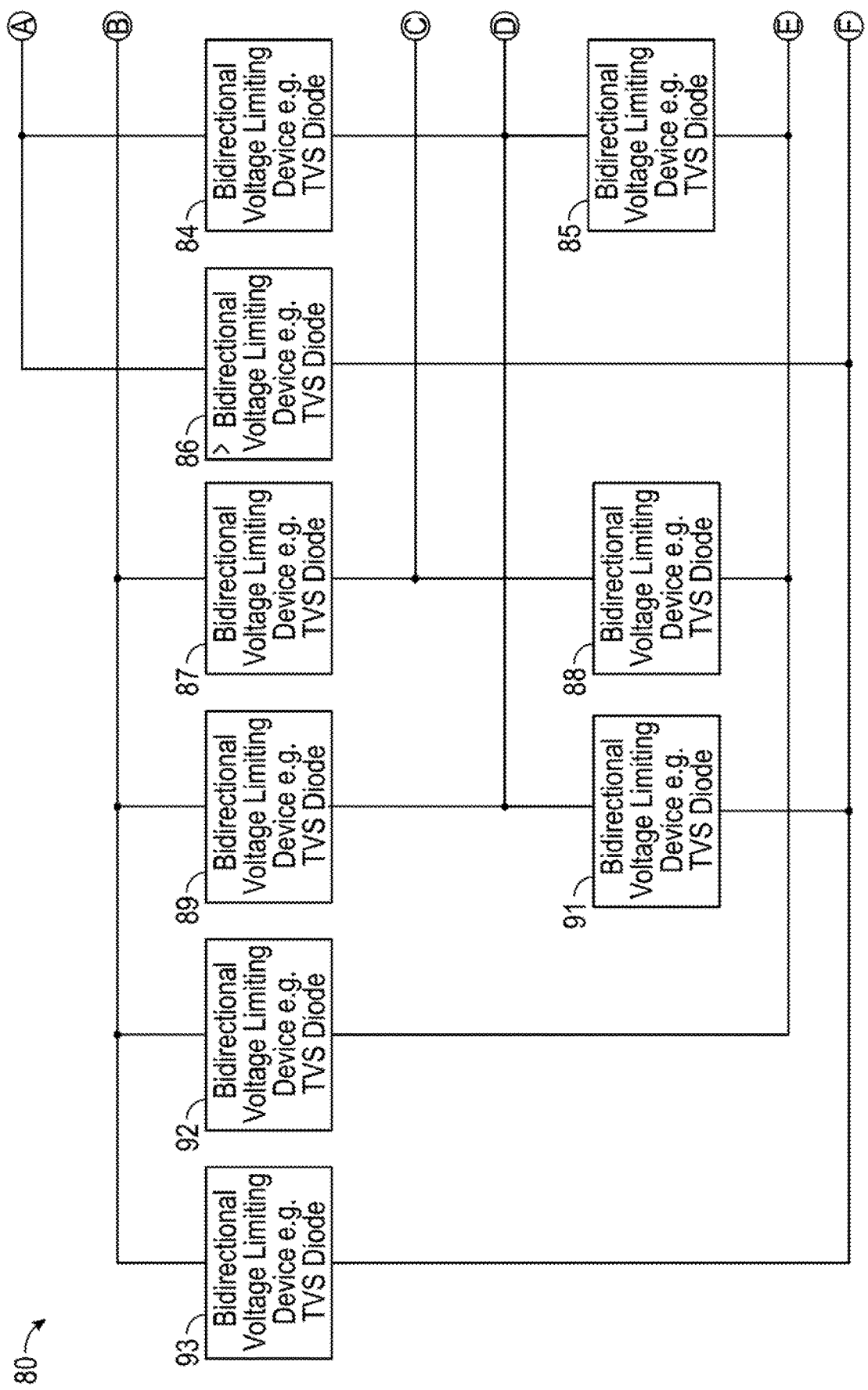
FIGS. 8A to 8D illustrate a further embodiment of an overvoltage protection circuit with six patient line interfaces.
Figure 8B:
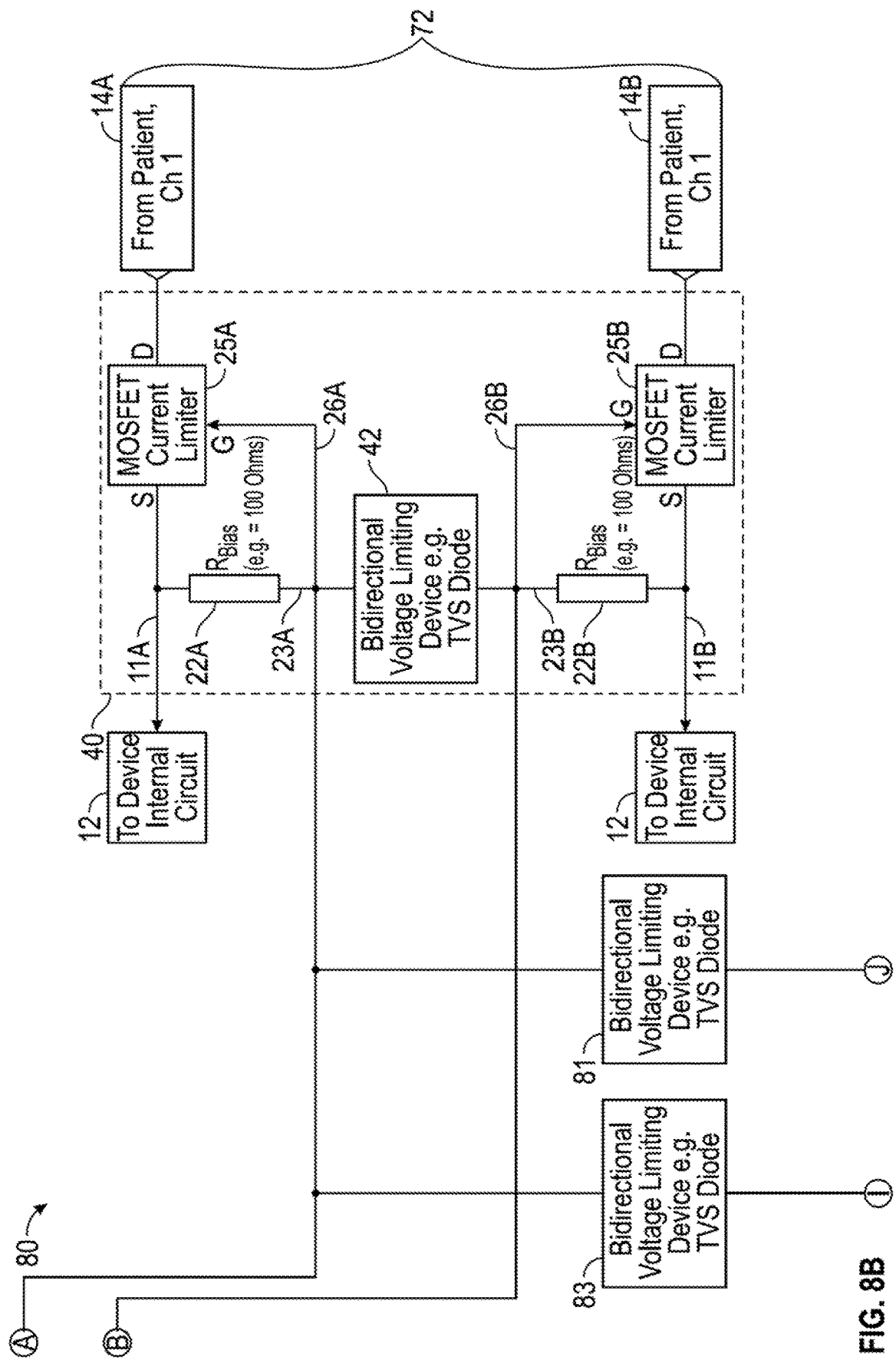
Figure 8C:
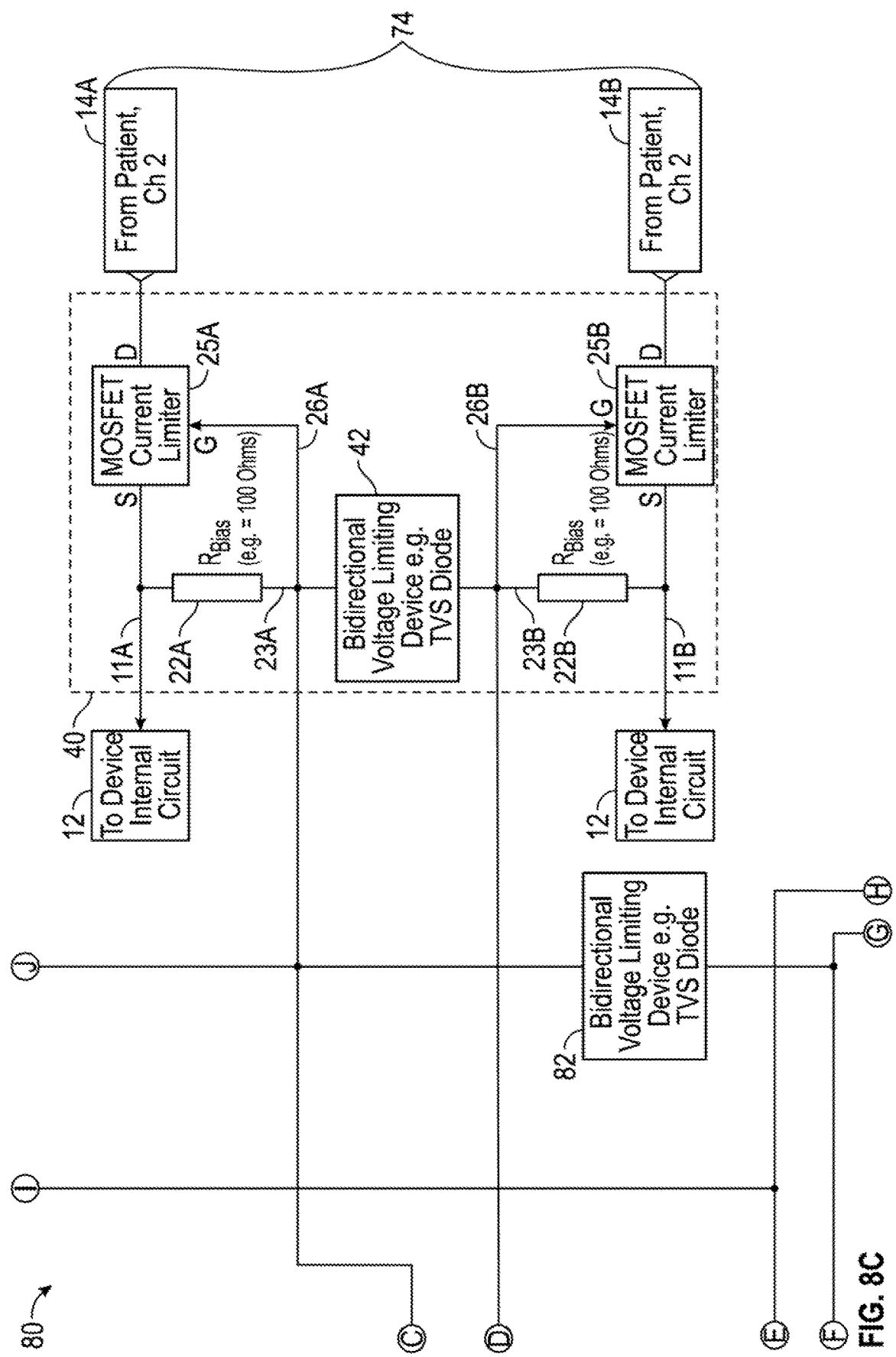
Figure 8D:
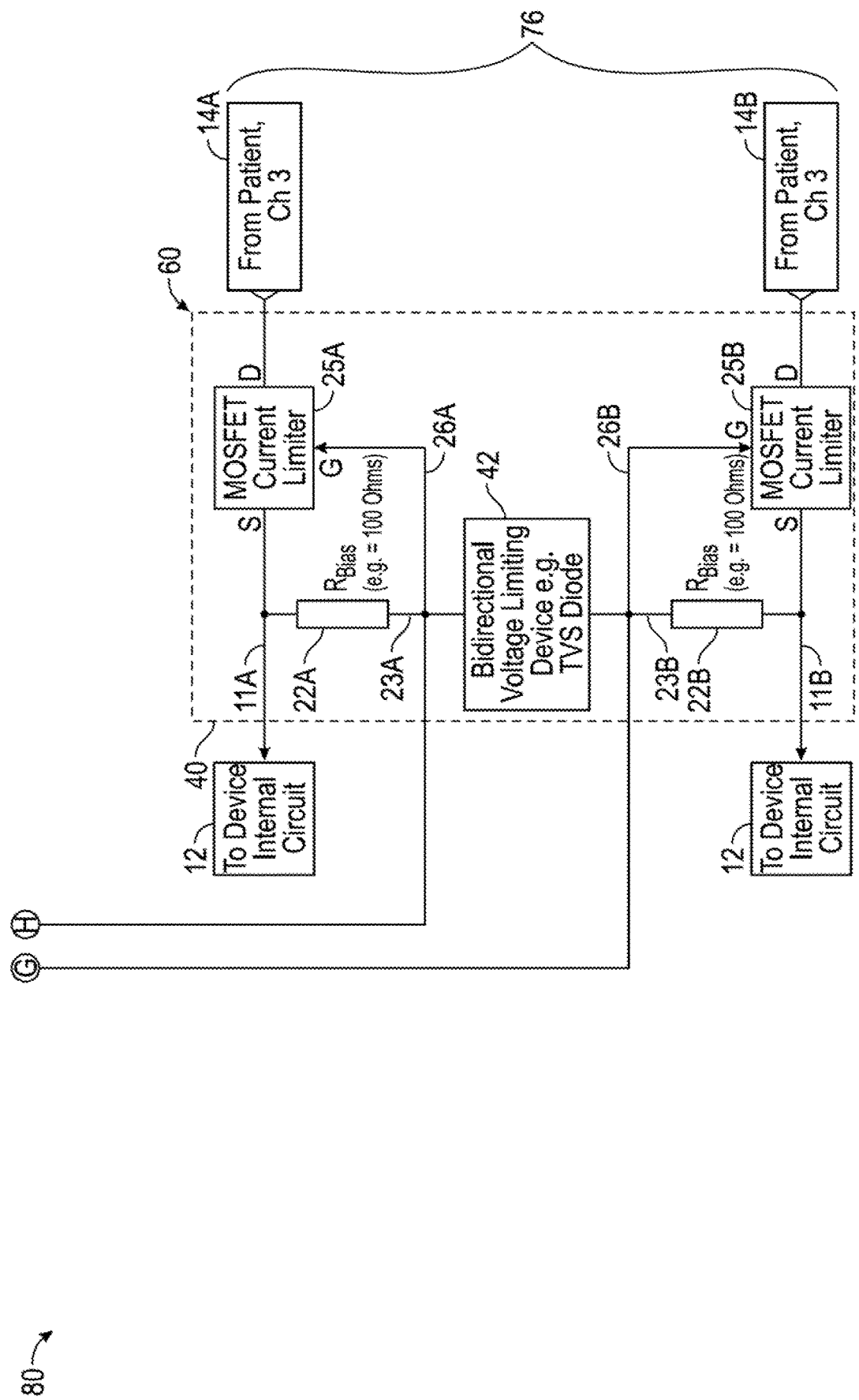
Figure 9A:
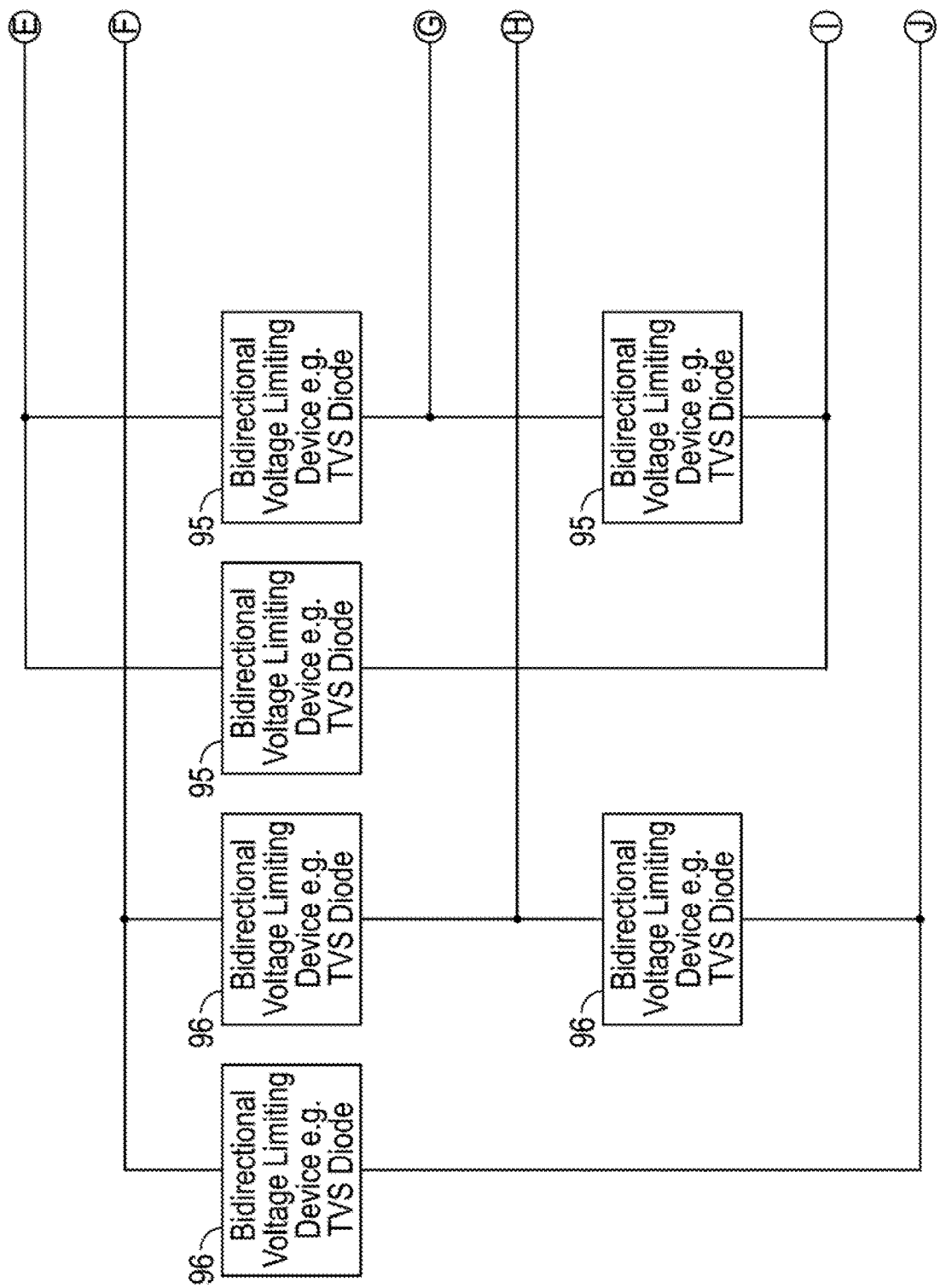
FIGS. 9A to 9D illustrates a further, more simplified embodiment of an overvoltage protection circuit with six patient line interfaces.
Figure 9B:
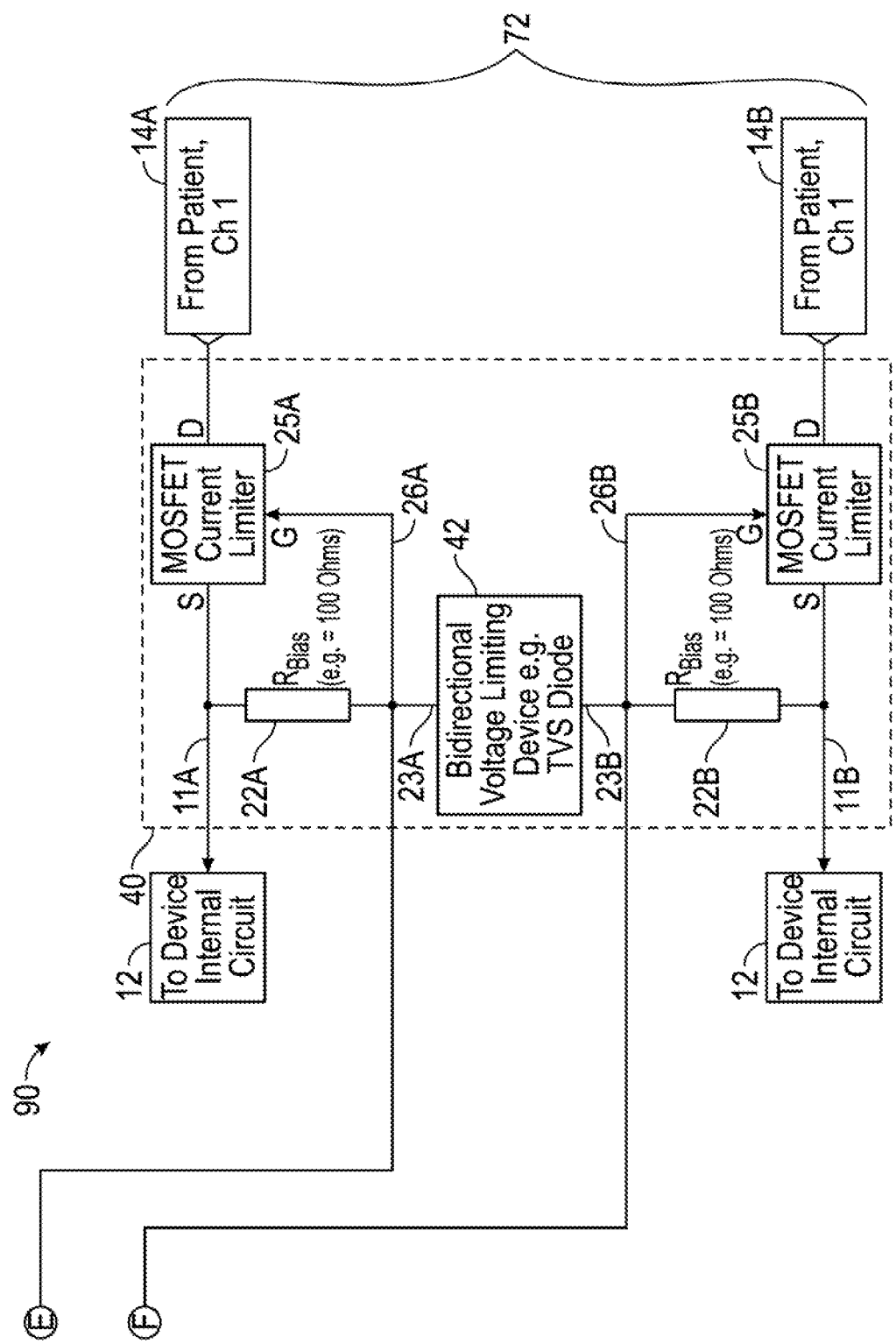
Figure 9C:
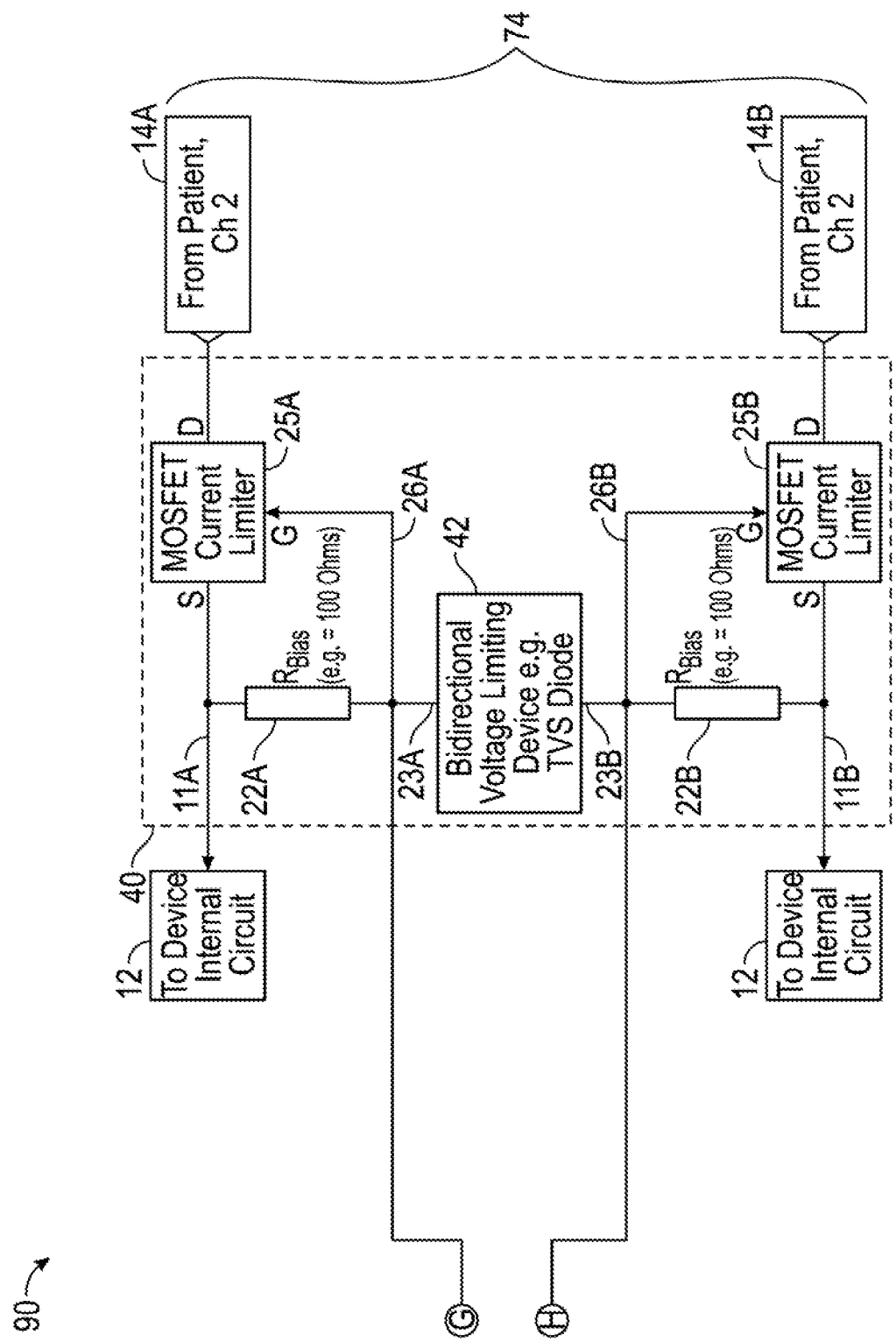
Figure 9D:
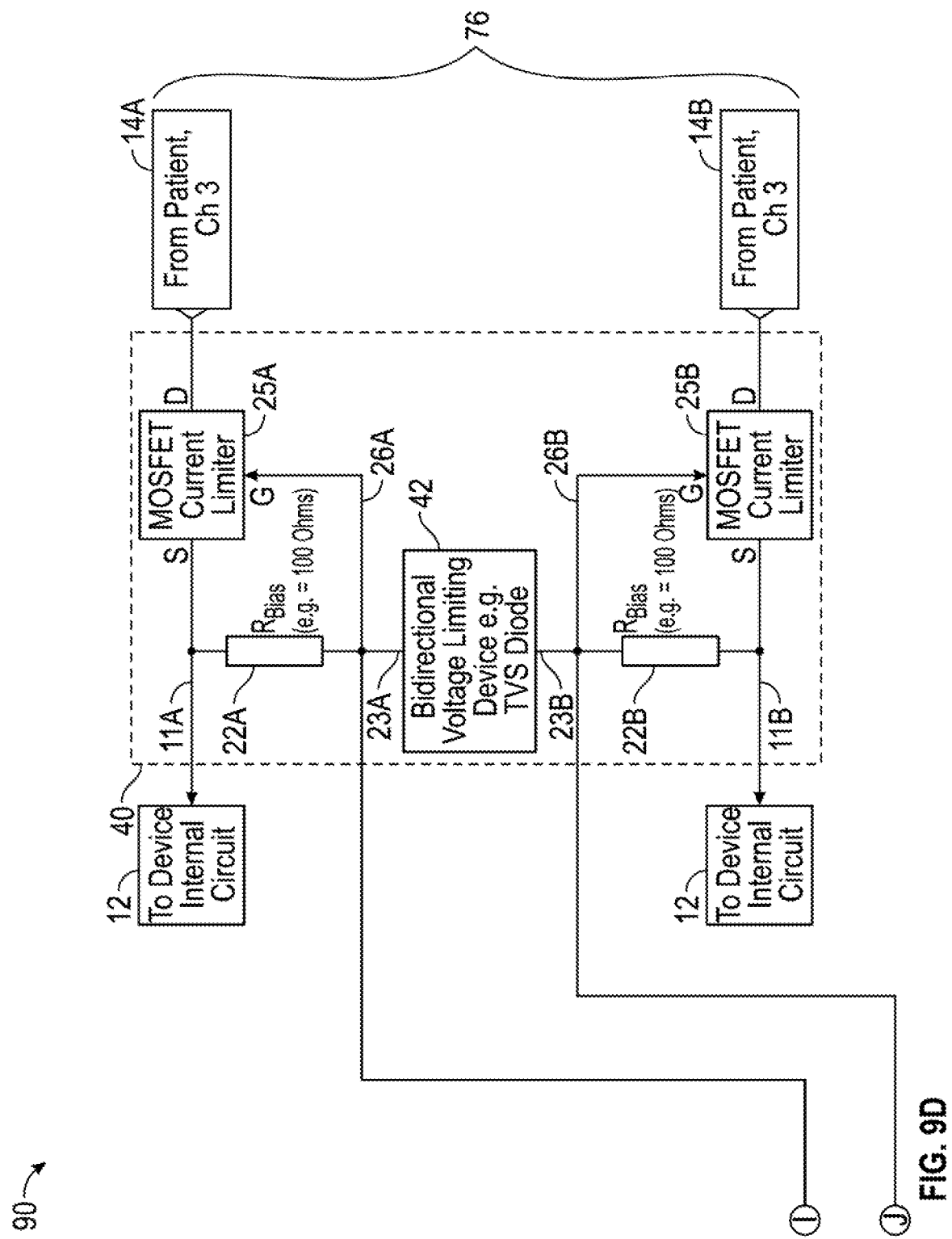

FIGS. 8A to 8D illustrate an embodiment of an overvoltage protection circuit 80 similar to that of FIGS. 6A and 6B but modified for protecting a three channel patient interface, and like reference numbers are used for like parts as appropriate. As in the previous embodiments, circuit 80 is arranged to generate a bias voltage using a resistor (impedance) having one end connected to the patient line interface, and in this case respective biasing resistors have first ends connected to the respective six patient line interfaces applicable, for instance, for the three patient channels of a triple-chamber pacemaker or a hemodynamic monitor with three patient channels 72 (FIG. 8B), 74 (FIG. 8C), and 76 (FIG. 8D). As in FIGS. 6A, 6B, this circuit employs a bidirectional TVS device 42 between biasing resistors 22A, 22B in each patient channel, along with additional bidirectional TVS devices between patient lines in different patient channels, as described in more detail below. This provides full overvoltage protection upon and during occurrence of overvoltage of any polarity between any pair of patient lines, including overvoltage occurring between patient lines in two different channels.

In order to achieve overvoltage protection for three channels with bidirectional transient voltage suppressors, it is not enough to apply one bi-directional TVS in each patient channel. In the illustrated embodiment, another twelve bidirectional transient voltage suppressors or TVS devices are connected between the three patient channels to activate the current limiting capability of this protection circuit in case a transient voltage occurs across patient lines belonging to different patient channels. In FIGS. 8A to 8D, a bidirectional TVS is connected between each pair of patient lines. The connecting lines are as follows:

TVS 81—Between biasing resistor 22A of channel 72 and biasing resistor 22A of channel 74 (see FIGS. 8B and 8C via J);

TVS 82—Between biasing resistor 22A of channel 74 and biasing resistor 22B of channel 76 (see FIGS. 8C and 8D via J);

TVS 83—Between biasing resistor 22A of channel 72 and biasing resistor 22A of channel 76 (see FIG. 8B, 8C, 8D via I, H);

TVS 84—Between biasing resistor 22A of channel 72 and biasing resistor 22B of channel 74 (see FIG. 8B, 8A, 8C via A, D);

TVS 85—Between biasing resistor 22B of channel 74 and biasing resistor 22A of channel 76 (see FIG. 8C, 8A, 8D via D, E, H);

TVS 86—Between biasing resistor 22A of channel 72 and biasing resistor 22B of channel 76 (see FIG. 8B, 8A, 8D via A, F, G);

TVS 87—Between biasing resistor 22B of channel 72 and biasing resistor 22A of channel 74 (See FIG. 8B, 8A, 8C via B, C);

TVS 88—Between biasing resistor 22A of channel 74 and biasing resistor 22A of channel 76 (See FIG. 8C, 8A, 8D via C, E, H);

TVS 89—Between biasing resistor 22B of channel 72 and biasing resistor 22B of channel 74 (See FIG. 8B, 8A, 8C via B, D);

TVS 91—Between biasing resistor 22B of channel 74 and biasing resistor 22B of channel 76 (See FIG. 8C, 8A, 8D via D, F, G);

TVS 92—Between biasing resistor 22B of channel 72 and biasing resistor 22A of channel 76 (See FIG. 8B, 8A, 8D via B, E, H);

TVS 93—Between biasing resistor 22B of channel 72 and biasing resistor 22B of channel 76 (See FIG. 8B, 8A, 8D via B, F, G)

The total number of bidirectional transient voltage suppressors (TVS) in circuit 80 is fifteen. This is significantly more than the embodiment of FIG. 7A to 7C using unidirectional TVS, where only six unidirectional TVS are required. However, since the TVS devices do not need to conduct large currents and thus do not need to be high power devices, tiny modern ESD protection TVS devices may be used in some embodiments. These devices are almost all bidirectional, so that the addition of ten more electronic components does not substantially increase size or expense of the device.

FIGS. 9A to 9D illustrates a simplified embodiment of an overvoltage protection circuit 90 for generating a bias voltage using a resistor (impedance) having a first end connected with the patient line interface for six patient line interfaces via respective lines extending off the respective line interfaces, and employing bi-directional TVS between biasing resistors in the respective patient channels. As in the two previous embodiments, this embodiment is applicable, for instance, for the three patient channels of a triple-chamber pacemaker.

Circuit 90 includes three of the overvoltage protection circuits 40 as shown in FIGS. 4, 6A and 6B applied to a three channel patient interface of a medical device having three patient channels 72, 74, 76 rather than two channels as in FIG. 6A, 6B, and like reference numbers are used for like parts as appropriate. Circuit 90 provides for a three channel patient interface similar to FIGS. 8A to 8D but with a simplified bidirectional TVS configuration. An example of where this circuit can be used is a bi-ventricular pacemaker. The circuit 90 provides full overvoltage protection for three channels, i.e. it protects the device upon and during occurrence of the overvoltage of each polarity between any of the six patient lines. As in FIGS. 8A to 8D, each patient channel 72, 74, 76 is equipped with one bidirectional transient voltage suppressor 42. However, there are only six bidirectional TVS elements 95, 96 between the patient channels instead of twelve bidirectional TVS elements as in FIGS. 8A to 8D. This is done at the expense of unequal TVS breakdown voltage. For some combinations of patient lines at which a voltage transient can be expected, the breakdown voltage UTVS is expected, whereas for some other patient line combinations the breakdown voltage is equal to 2 UTVS. However, this is not a problem in providing protection capabilities of the protection circuit in many cases where UTVS is still only a fraction of the likely voltage transients which may occur. In FIGS. 9A to 9D, a respective bidirectional TVS 95 is connected between the biasing diodes 22A in each pair of circuits 40 (see E, G, I) and a respective bidirectional TVS 96 is connected between the biasing diodes 22B in each pair of circuits 40 (see F, H, J) making a total of six bidirectional TVS devices. However, unlike FIGS. 8A to 8D, there are no bidirectional TVS elements between a biasing diode 22A in one circuit and a biasing diode 22B in either of the other two circuits, which eliminates six of the bidirectional TVS elements of FIGS. 8A to 8D.

The three channel overvoltage protection circuits of FIGS. 7A to 9D may be scaled up for a four channel medical device such as a heart monitor or pacemaker for the four chambers of the heart by adding an additional circuit 30 or 40 for the fourth channel in a similar manner to channels 72, 74 and 76 of FIGS. 7A to 9D, and additional bidirectional TVS devices between patient lines in each channel when one bidirectional TVS rather than two unidirectional TVS devices is used between the biasing resistors in each patient channel, as in FIG. 8A to 8D or 9A to 9D.

Figure 10:
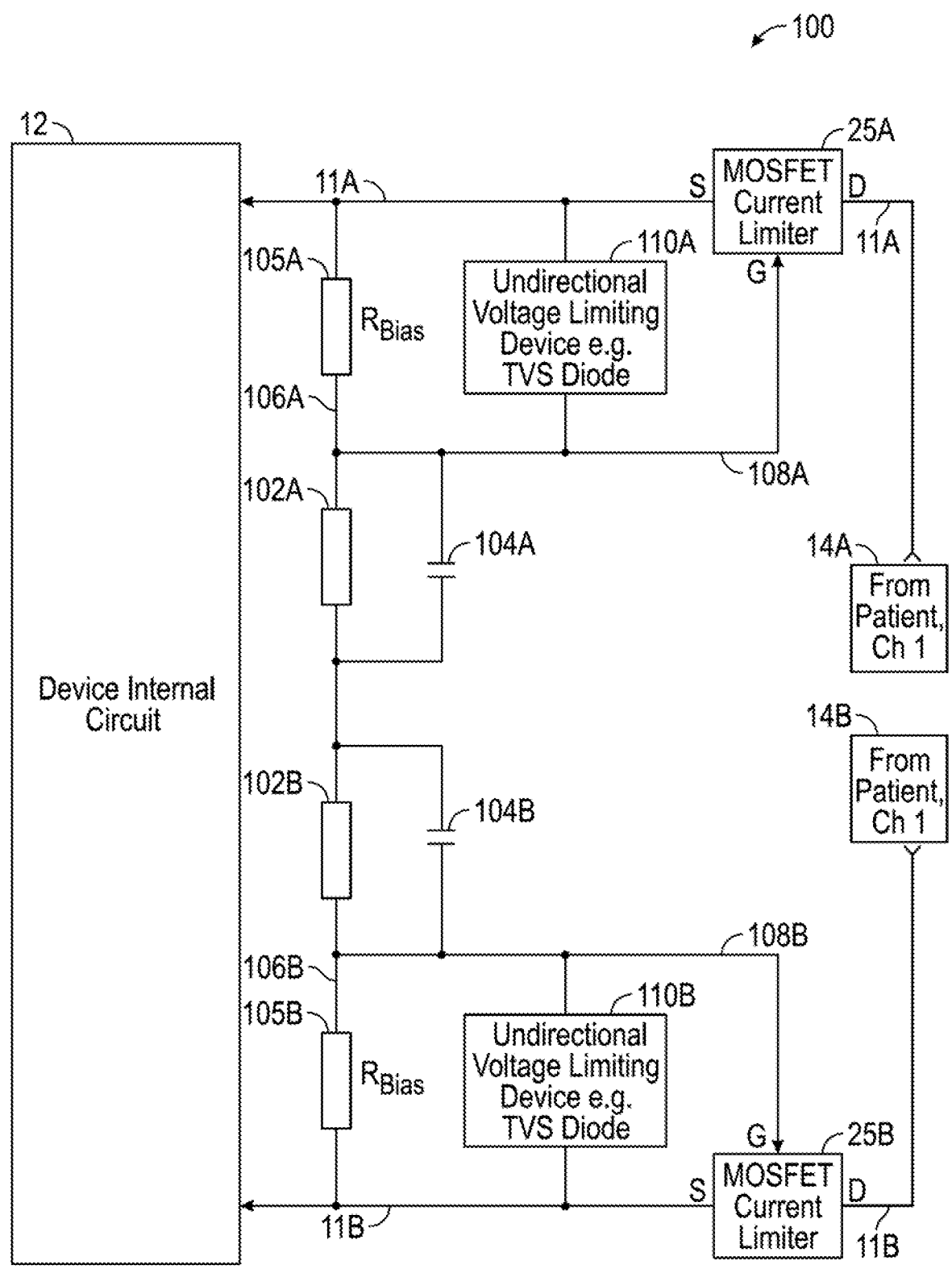
FIG. 10 illustrates another embodiment of an overvoltage protection circuit.

FIG. 10 illustrates another embodiment of an overvoltage protection circuit 100 for two patient line interfaces or one patient channel of an electrical medical device. The circuit 100 is connected between the device internal circuit 12 and the patient interfaces of the medical device. In this embodiment, the transient voltage suppressor or TVS elements are replaced with a respective resistor 102A, 102B in parallel with a respective compensation capacitor 104A, 104B and connected in series with a biasing resistor 105A or 105B which is connected at one end to a respective patient line 11A or 11B, as seen in FIG. 10. In some embodiments, compensation capacitors 104A and 104B may be omitted. As in the previous embodiments, each patient line 11A, 11B includes a MOSFET current limiter 25A, 25B. The junction 106A between resistor 105A and resistor 102A is connected to the gate of MOSFET 25A via line 108A. Similarly, junction 106B is connected to the gate of MOSFET 25B via line 108B. Respective unidirectional voltage limiting devices or TVS diodes 110A, 110B are connected in parallel with respective biasing resistors 105A, 105B between patient line 11A, 11B and line 108A, 108B, respectively. The unidirectional voltage limiting device 110A is connected with its anode tied to the patient line 11A and its cathode tied to the junction 106A, and the unidirectional voltage limiting device 110B is connected with its anode tied to the patient line 11B and its cathode tied to the junction 106B.

Overvoltage protection circuit 100 provides protection for two patient lines 11A, 11B, which constitute one patient channel, and utilizes current limiter devices 25A, 25B (built with depletion mode MOSFETs or the like) employed in exactly the same way as in the previous embodiments shown in FIG. 2 to FIG. 9D. However, in this embodiment, the biasing voltage is obtained from a first resistive voltage divider comprising resistors 105A and 102A and a second resistive voltage divider comprising resistors 105B and 102B built between the two patient lines. Upon an occurrence of the first ramp of an overvoltage, initially a small current flows through the resistors of the voltage divider. Once the voltage across one of the biasing resistors 105A or 105B reaches the required bias level of the MOSFET, the respective MOSFET shuts off the current flow through the patient lines. Which MOSFET turns off first depends on the direction of the transient overvoltage. The voltage divider can be adjusted in such a way that the shut off of the MOSFET happens even more quickly than is the case in the overvoltage protection circuits from FIG. 2 to FIG. 9D. In one example, resistors 105A and 105B may each have a resistance of 10 KOhms, while resistors 102A, 102B may each have a resistance of 22 KOhms and capacitors 104A, 104B each have a capacitance of 10 nF (nanofarads). The resistance of resistors 105A and 105B may be in a range of 10 kOhm to 1 MOhm, whereas the range of suitable resistances of resistors 102A and 102B is from 22 kOhm to 3.3 MOhm. The compensation capacitors 104A and 104B may have a capacitance of a few picofarads to 22 nF (nanofarads). The actual values strongly depend on properties of patient lines of the device with which the overvoltage protection circuit is used.

The voltage divider can be built of high ohmic resistors, so that the current through each resistor pair 105A, 102A and 105B, 102B is in consequence very small. However, during the dimensioning procedure of the voltage divider, care should be taken with regard to the MOSFET capacitance Ciss seen at the MOSFET gate terminal G, since this capacitance, together with the biasing resistor 105A or 105B, forms a low pass filter. Ciss is the sum of the gate-to-source capacitance and the gate-to-drain capacitance (Ciss=Cgs+Cgd). Depending on the particular MOSFET used in the circuit, this capacitance can have the value of up to some nanofarads. In order to compensate for this, respective compensation capacitors 104A, 104B are applied in parallel with the respective resistors 102A, 102B. In some embodiments, it may be best to arrange the compensation capacitor to overcompensate for Ciss, since this makes the response to an overvoltage transient faster than in case of exact compensation. However, the introduction of the capacitors 104A, 104B influences the frequency response of the protection circuit. With the component parameters in the above example used in the embodiment of FIG. 10, the −3 dB attenuation limit is achieved at about 25 kHz. Such a frequency response is fully sufficient for most biological signals when the overvoltage protection device is used in pacemaker devices or ECG monitors. In embodiments for protection of hemodynamic monitors, the circuit parameters may be changed so that the circuit introduces less attenuation. For patient channels of hemodynamic monitors responsible for voltage measurement the value of the compensation capacitor may be reduced to a pF (picofarad) value or the compensation capacitor may be omitted entirely. This is possible, since voltage measurement patient channels do not exhibit impedance which is as low as pacemaker channels or current channels of hemodynamic monitors.

Circuit 100 includes TVS elements 110A and 110B connected across the gate and source terminals of the respective the MOSFET current limiters 25A, 25B to protect against an excessive voltage between the gate and source terminals. It should however be noted that the TVS elements used in this circuit do not introduce any voltage limiting capability to patient lines. The only purpose of the TVS elements in circuit 100 is to protect the MOSFET current limiters against an excessive gate-source voltage, which may cause damage to the MOSFET. The voltage limitation of overvoltage protection circuit 100 is achieved alone through the shutting off of MOSFETs 25A and 25B as described above. The desired shut off effect is in turn strongly dependent on the appropriate dimensioning of the voltage divider mentioned above.

The overvoltage protection circuit presented in FIG. 10 has two advantages compared to the circuit shown in FIG. 2 and FIGS. 3 to 9D. The first advantage is higher sensitivity to overvoltage transient events and the second advantage is a better controllable and much deeper shut off of MOSFETs. This in turn leads to a better rejection of energy delivered by a transient event, and improved energy rejection capability. However, the overvoltage protection in this embodiment is more dependent on correct dimensioning or component parameters than the previous embodiments. The dimensioning in turn is more dependent on the particular medical equipment to which the overvoltage protection circuit is applied.

Figure 11A:
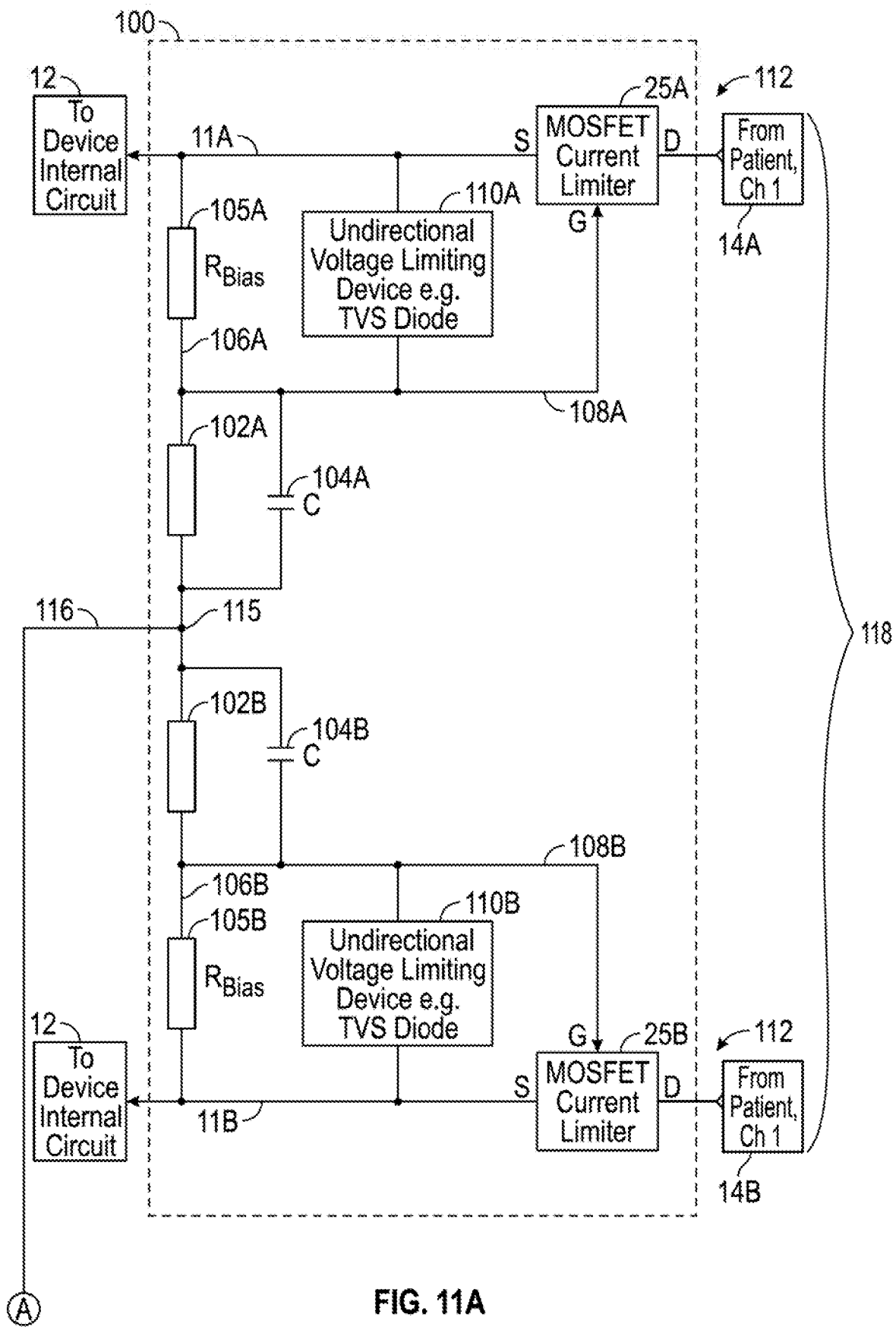
FIGS. 11A and 11B illustrate a modification of the circuit of FIG. 10 to provide overvoltage protection for two patient channels of a medical device.
Figure 11B:
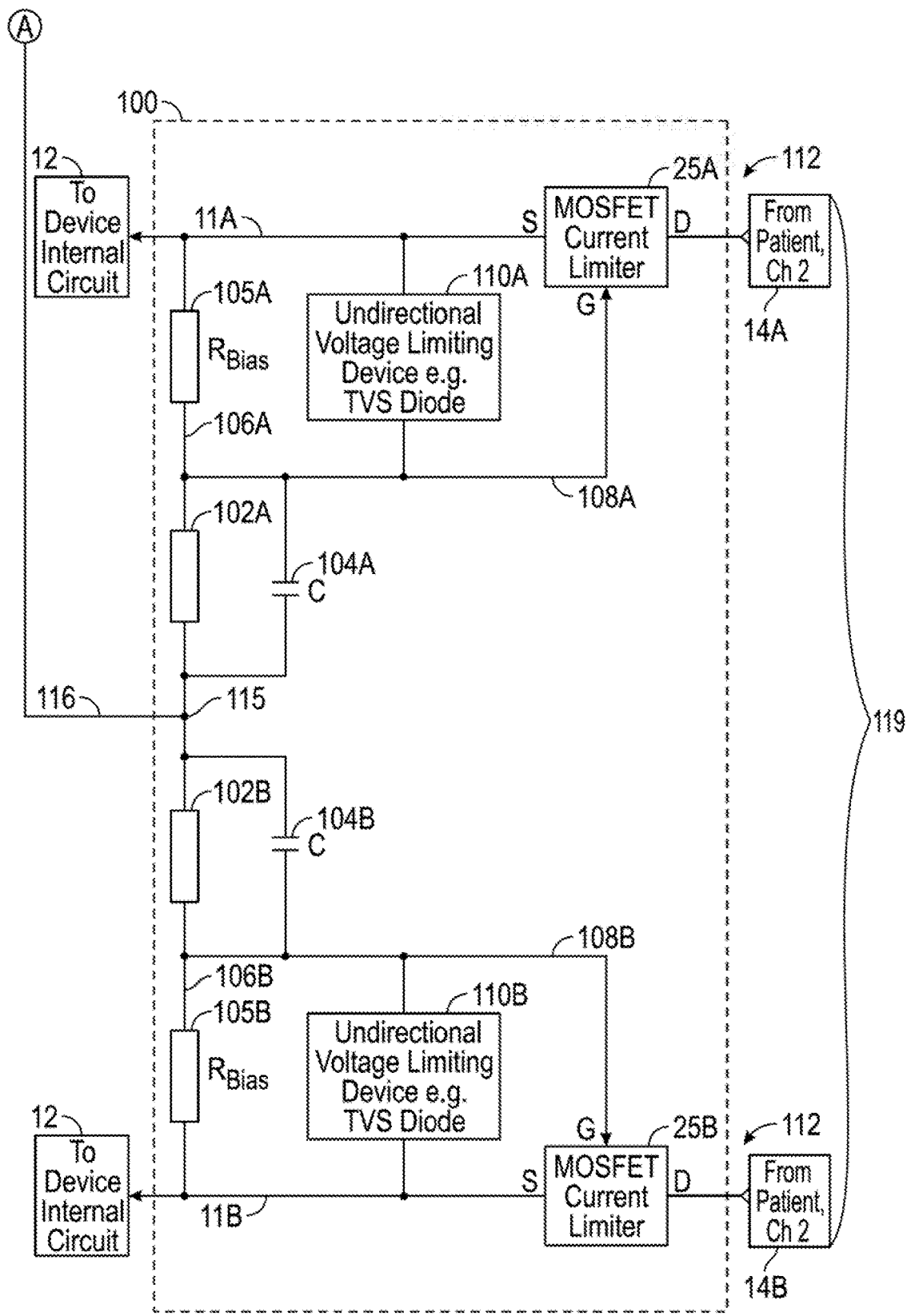

FIGS. 11A and 11B illustrate one embodiment of a modified overvoltage protection circuit or device 112 which uses the same overvoltage protection technique as FIG. 10 to provide overvoltage pulse protection for an electronic medical device having two patient channels 118 (FIG. 11A) and 119 (FIG. 11B), such as a dual-chamber pacemaker, or two channels of a hemodynamic monitor. Device 120 comprises two of the single channel circuits 100 of FIG. 10 applied to the respective channels 118, 119 of a dual channel device, and like reference numbers are used for like parts as appropriate. As in FIG. 10, the circuit 100 of each channel has a first biasing resistor 105A connected at one end to the patient line 11A and connected in series with first resistor 102A, which in turn is connected in parallel with compensation capacitor 104A. The junction 106A between resistors 102A and 105A is connected via line 108A to the gate of MOSFET 25A in patient line 11A. Each second biasing resistor 105B is connected at one end to patient line 11B and in series with second resistor 102B connected in parallel with compensation capacitor 104B. The junction 106B between resistors 102B and 105B is connected via line 108B to the gate of MOSFET 25B located in patient line 11B. Additionally, the junctions 115 between voltage limiting devices 102A and 102B in each circuit are connected together by line 116.

Examples of medical devices where circuit 112 may be used are a dual chamber pacemaker or two channels of a hemodynamic monitor. Circuit 112 provides overvoltage protection for the two channels, i.e. it protects the medical device upon and during occurrence of the overvoltage of each polarity between any patient lines and reduces or eliminates the risk of the device absorbing the energy contained in the overvoltage.

In one example of two channel overvoltage protection circuit 112, resistors 105A and 105B may each have a resistance of 470 kOhms, while resistors 102A, 102B may each have a resistance of 1.5 MOhms and capacitors 104A, 104B each have a capacitance of 10 nF.

Figure 12A:
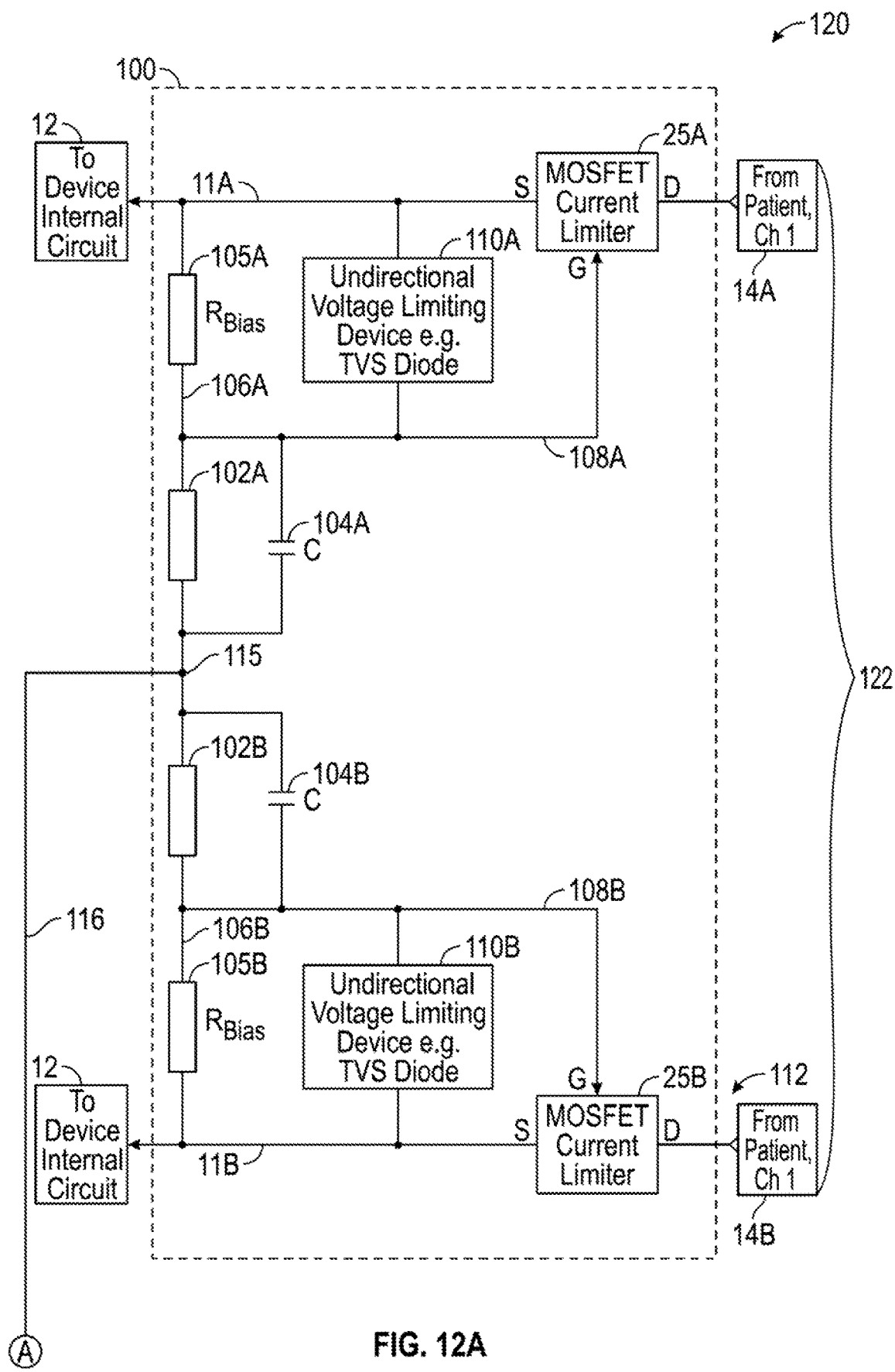
FIGS. 12A to 12C illustrate a modification of the circuits of FIGS. 10 to 11B to provide overvoltage protection on three patient channels.
Figure 12B:
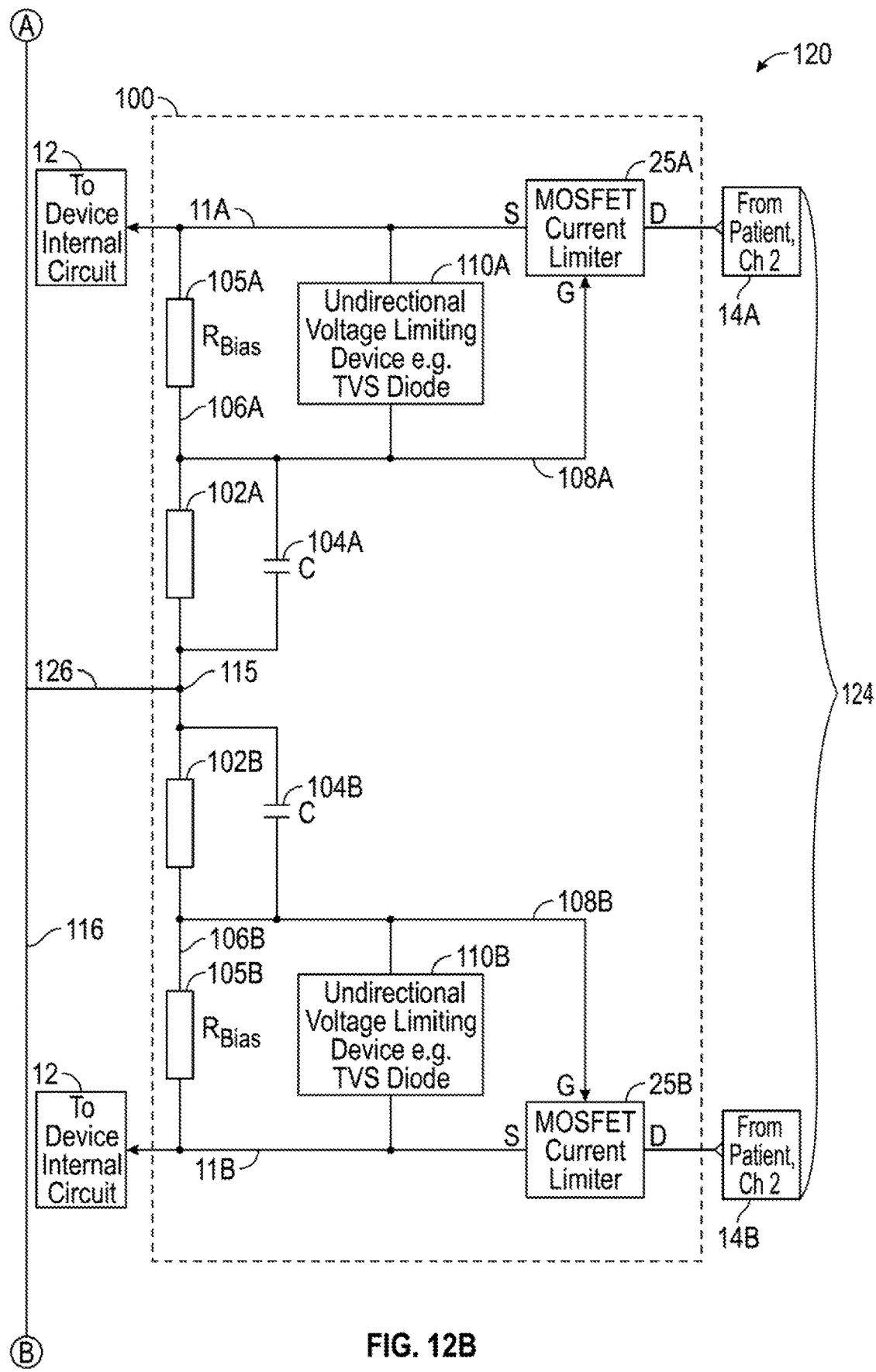
Figure 12C:
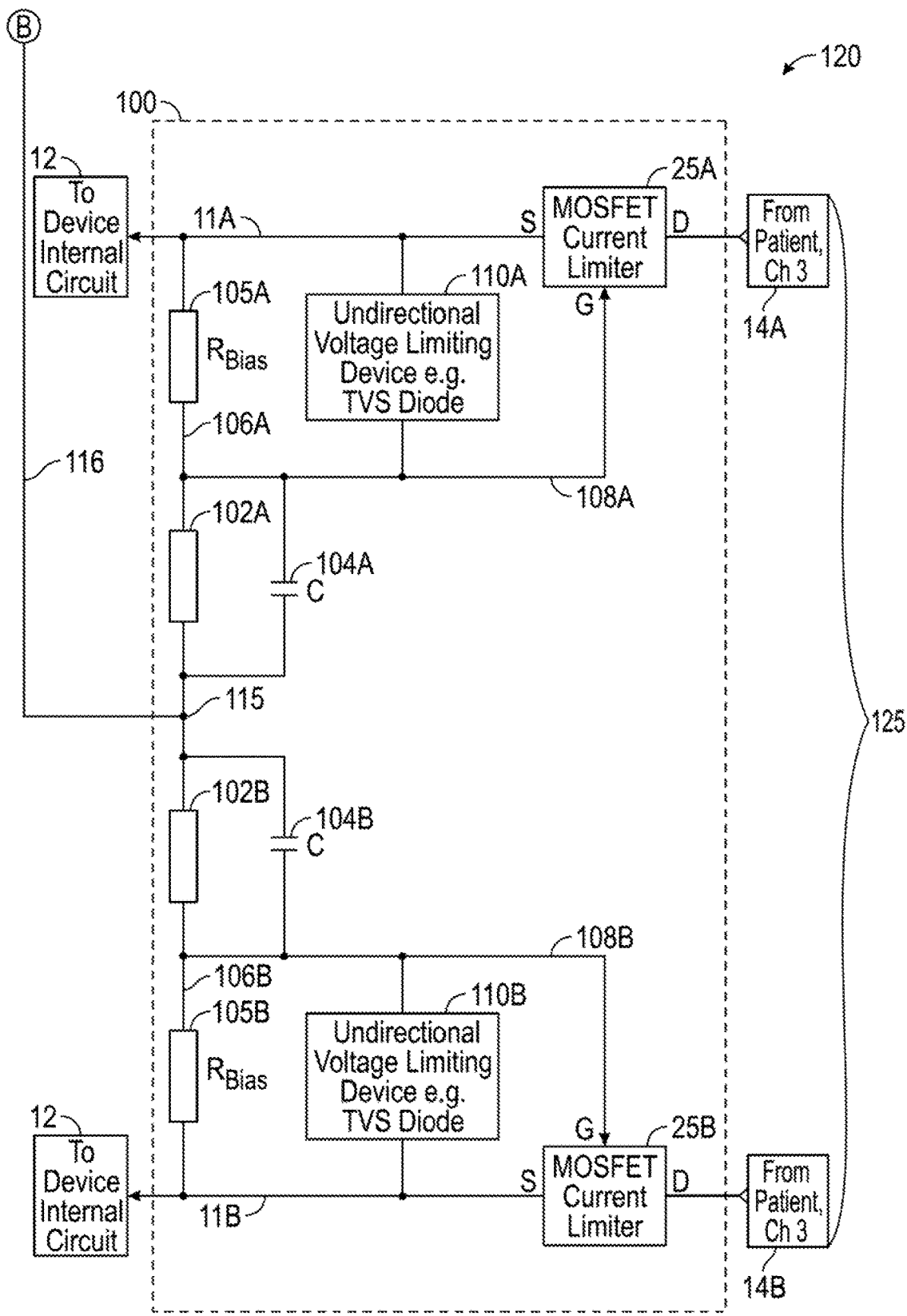

FIGS. 12A to 12C illustrates one embodiment of a modified overvoltage protection circuit or device 120 similar to FIGS. 10, 11A and 11B which is configured to provide overvoltage pulse protection for an electronic medical device having three patient channels 122 (FIG. 12A), 124 (FIG. 12B), 125 (FIG. 12C), such as a triple-chamber pacemaker or a hemodynamic monitor with three channels.

Device 120 comprises three of the single channel circuits 100 of FIG. 10 applied to the respective channels 122, 124 and 125 of a three channel device, and like reference numbers are used for like parts as appropriate. As in FIG. 10, the circuit 100 of each channel has a first biasing resistor 105A connected at one end to line 11A and in series with first resistor 102A connected in parallel with compensation capacitor 104A. The junction 106A between resistors 102A and 105A is connected via line 108A to the gate of MOSFET 25A in patient line 11A. A TVS diode 110A is connected between lines 11A and 108A in parallel with biasing resistor 105A. Each second biasing resistor 105B is connected at one end to the respective patient line 11B and in series with second resistor 102B connected in parallel with compensation capacitor 104B. The junction 106B between resistors 102B and 105B is connected via line 108B to the gate of MOSFET 25B located in patient line 11B. A TVS diode 110B is connected between lines 11B and 108B in parallel with biasing resistor 105B. Additionally, the junctions 115 between voltage limiting devices 102A and 102B in each circuit are connected together by lines 116 and 126.

The modified overvoltage protection circuit 120 of FIGS. 12A to 12C is designed for protecting a three channel patient interface by generating a bias voltage using respective resistors (impedance) each connected at one end to the respective patient line of each of the six patient lines 11A, 11B. This device is applicable, for instance, for the three patient channels of a triple-chamber pacemaker or a hemodynamic monitor. In one example of three channel overvoltage protection circuit 120, resistors 105A and 105B may each have a resistance of 470 kOhms, while resistors 102A, 102B may each have a resistance of 1.5 MOhms and capacitors 104A, 104B each have a capacitance of 10 nF.

Although the overvoltage protection circuits and methods above are described as providing overvoltage protection for an electrical or electronic medical device, they may alternatively be used to protect other types of circuits against accidental overvoltages between two terminals. In some embodiments, the overvoltage protection circuit may be incorporated in the medical device internal circuit itself or be provided for connection to patient output/input terminals or channels of an existing medical device. The overvoltage protection circuits described above may be used in conjunction with any electrical medical devices used for treatment or monitoring purposes in or on the body (human or animal).

The above description of the disclosed embodiments is provided to enable any person skilled in the art to make or use the invention. Various modifications to these embodiments will be readily apparent to those skilled in the art, and the generic principles described herein can be applied to other embodiments without departing from the spirit or scope of the invention. Thus, it is to be understood that the description and drawings presented herein represent a presently preferred embodiment of the invention and are therefore representative of the subject matter which is broadly contemplated by the present invention. It is further understood that the scope of the present invention fully encompasses other embodiments that may become obvious to those skilled in the art and that the scope of the present invention is accordingly limited by nothing other than the appended claims.

What is claimed is:

1. An overvoltage protection device, comprising:
   a first line for connection between first and second terminals, wherein the first line is a first patient line of a medical device, the first terminal communicates with an internal circuit of the medical device, and the second terminal comprises a patient interface;
   a current limiting device connected in the first line between the first terminal and second terminal, the current limiting device having an on state and an off state and being configured to limit current passing through the current limiting device between the first and second terminals when in the off state, the current limiting device configured to switch from the on state to the off state, in response to a predetermined biasing voltage, to thereby shut off current flow through the first line;
   a second line extending off the first line;
   a biasing voltage generating circuit connected in the second line and comprising at least one biasing element and at least one additional circuit element connected in series with the biasing voltage generating device, the biasing element and additional circuit element configured to apply a predetermined biasing voltage to the current limiting device in response to a transient overvoltage on the first line, whereby the current limiting device is switched off to shut off current flow through the first line;
   a second patient line, the first and second patient lines comprising a patient channel, a second patient interface at one end of the second patient line and the opposite end of the second patient line communicating with the internal circuit of the medical device, a second current limiting device connected in the second patient line between the second patient interface and the internal circuit of the medical device, the second line extending between the first and second patient lines and the biasing voltage generating circuit further comprising at least a second biasing element in the second line, the second biasing element configured to apply a predetermined biasing voltage to the second current limiting device in response to a transient overvoltage on the second patient line, whereby the second current limiting device is switched off and limits current flow through the second patient line;
   a second patient channel having first and second patient lines and having opposite first and second ends, the respective first ends being in communication with the internal circuit of the medical device, and the second ends comprising respective first and second patient interfaces, respective first and second current limiting devices in the first and second patient lines of the second patient channel, and a second biasing voltage generating circuit identical to the first mentioned biasing voltage generating circuit connected in a second line extending between the first and second patient lines of the second patient channel and configured for generating a bias voltage to turn off at least the respective first or second current limiting device of the second patient channel in the event of a transient voltage pulse in the first or second patient lines, respectively, of the second patient channel;
   a third patient channel having first and second patient lines and having opposite first and second ends, the respective first ends being in communication with the internal circuit of the medical device, and the second ends comprising respective first and second patient interfaces, respective first and second current limiting devices in the first and second patient lines of the third patient channel, and a third biasing voltage generating circuit identical to the first mentioned and second biasing voltage generating circuits and configured for generating a bias voltage to turn off at least the respective first or second current limiting device of the third patient channel in the event of a transient voltage pulse in the first or second patient lines, respectively, of the third patient channel; and a connecting link forming a connection between the bias voltage generating circuits of the first, second, and third patient channels, wherein the connecting link provides a connection between a first location between the first and second bias voltage generating circuits of the first patient channel, a second location between the first and second bias voltage generating circuits of the second patient channel, and a third location between the first and second bias voltage generating circuits of the third patient channel.

2. The device of claim 1, wherein the at least one additional circuit element is connected between the first and second biasing elements.

3. The device of claim 2, wherein the biasing elements comprise first and second biasing resistors.

4. The device of claim 3, wherein each biasing resistor has a resistance in the range from 50 Ohms to 1 kOhm.

5. The device of claim 3 wherein the additional circuit element comprises at least one voltage limiting device connected between the first and second biasing resistors.

6. The device of claim 5, wherein the current limiting devices comprise first and second depletion mode metal-oxide-semiconductor field-effect transistors (MOSFETs).

7. The device of claim 5, wherein the at least one voltage limiting device comprises a transient voltage suppressor (TVS).

8. The device of claim 7, wherein a single bidirectional TVS is connected between the first and second biasing voltage generating devices.

9. The device of claim 7, wherein the voltage limiting devices comprise a first unidirectional TVS connected to a second end of the first biasing resistor and a second unidirectional TVS connected between the first unidirectional TVS and a second end of the second biasing resistor.

10. The device of claim 6, wherein each MOSFET has a drain terminal connected to the second terminal, a source terminal in communication with the internal circuit of the medical device, and a gate terminal, the first biasing resistor is connected to the gate terminal of the first MOSFET, and the second biasing resistor is connected to the gate terminal of the second MOSFET.

11. The device of claim 3, wherein the at least one additional circuit element comprises a first resistor connected in series with the first biasing resistor to form a first voltage divider and a second resistor connected in series with the second biasing resistor to form a second voltage divider, a first junction between the first biasing resistor and first resistor connected to the first current limiting device and a second junction between the second biasing resistor and second resistor connected to the second current limiting device.

12. The device of claim 1, further comprising at least one connecting line having a first end connected at a location between the first and second bias voltage generating circuits of the first patient channel and a second end connected at a location between the first and second bias voltage generating circuits of the second patient channel.

13. The device of claim 12, wherein the first and second biasing elements of the bias voltage generating circuits of the first and second patient channels comprise biasing resistors and the additional circuit element comprises at least one voltage limiting device connected between the biasing resistors.

14. The device of claim 13, wherein the at least one additional circuit element comprises first and second unidirectional voltage limiting devices connected between the biasing resistors of each patient channel, and the connecting line has a first end connected at a first location between the first and second unidirectional voltage limiting devices of the first patient channel and a second end connected at a second location between the first and second unidirectional voltage limiting devices of the second patient channel.

15. An overvoltage protection device comprising:
a first line for connection between first and second terminals, wherein the first line is a first patient line of a medical device, and the first terminal communicates with an internal circuit of the medical device and the second terminal comprises a patient interface;
a current limiting device connected in the first line between the first terminal and second terminal, the current limiting device having an on state and an off state and being configured to limit current passing through the current limiting device between the first and second terminals when in the off state, the current limiting device configured to switch from the on state to the off state in response to a predetermined biasing voltage; and
a second line extending off the first line;
a biasing voltage generating circuit connected in the second line and comprising at least one biasing element and at least one additional circuit element connected in series with the biasing voltage generating device, the biasing element and additional circuit element configured to apply a predetermined biasing voltage to the current limiting device in response to a transient overvoltage on the first line, whereby the current limiting device is switched off and limits current flow through the first line;
a second patient line, the first and second patient lines comprising a patient channel;
a second patient interface at one end of the second patient line and the opposite end of the second patient line communicating with the internal circuit of the medical device;
a second current limiting device connected in the second patient line between the second patient interface and the internal circuit of the medical device, the second line extending between the first and second patient lines and the biasing voltage generating circuit further comprising at least a second biasing element in the second line, the second biasing element configured to apply a predetermined biasing voltage to the second current limiting device in response to a transient overvoltage on the second patient line, whereby the second current limiting device is switched off and limits current flow through the second patient line;
a second patient channel having first and second patient lines and having opposite first and second ends, the respective first ends being in communication with the internal circuit of the medical device, and the second ends comprising respective first and second patient interfaces, respective first and second current limiting devices in the first and second patient lines of the second patient channel;
a second biasing voltage generating circuit identical to the first mentioned biasing voltage generating circuit connected in a second line extending between the first and second patient lines of the second patient channel and configured for generating a bias voltage to turn off at least the respective first or second current limiting device of the second patient channel in the event of a transient voltage pulse in the first or second patient lines, respectively, of the second patient channel; and at least one connecting line having a first end connected at a location between the first and second bias voltage generating circuits of the first patient channel and a second end connected at a location between the first and second bias voltage generating circuits of the second patient channel;

wherein the first and second biasing elements of the bias voltage generating circuits of the first and second patient channels comprise biasing resistors and the additional circuit element comprises at least one voltage limiting device connected between the biasing resistors, and wherein the additional circuit element in each patient channel comprises a first bidirectional voltage limiting device connected between the biasing resistors in the respective patient channel, first and second junctions in each patient channel are located between the first biasing resistor and the bidirectional voltage limiting device and between bidirectional voltage limiting device and second biasing resistor, respectively, a first current path extends between the first junction in the first patient channel and the second junction in the second patient channel and a second bidirectional voltage limiting device is located in the first current path, a second current path extends between the first junction in the first patient channel and the first junction in the second patient channel and a third bidirectional voltage limiting device is located in the second current path, a third current path extends between the second junction in the first patient channel and the first junction in the second patient channel and a fourth bidirectional voltage limiting device is located in the third current path, a fourth current path extends between the second junction in the first patient channel and the second junction in the second patient channel and a fifth bidirectional voltage limiting device is located in the fourth current path.

16. An overvoltage protection device comprising:
a first line for connection between first and second terminals, wherein the first line is a first patient line of a medical device, the first terminal communicates with an internal circuit of the medical device and the second terminal comprises a patient interface;
a current limiting device connected in the first line between the first terminal and second terminal, the current limiting device having an on state and an off state and being configured to limit current passing through the current limiting device between the first and second terminals when in the off state, the current limiting device configured to switch from the on state to the off state in response to a predetermined biasing voltage;
a second line extending off the first line;
a biasing voltage generating circuit connected in the second line and comprising at least one biasing element and at least one additional circuit element connected in series with the biasing voltage generating device, the biasing element and additional circuit element configured to apply a predetermined biasing voltage to the current limiting device in response to a transient overvoltage on the first line, whereby the current limiting device is switched off and limits current flow through the first line;
a second patient line, the first and second patient lines comprising a patient channel;
a second patient interface at one end of the second patient line and the opposite end of the second patient line communicating with the internal circuit of the medical device;
a second current limiting device connected in the second patient line between the second patient interface and the internal circuit of the medical device, the second line extending between the first and second patient lines and the biasing voltage generating circuit further comprising at least a second biasing element in the second line, the second biasing element configured to apply a predetermined biasing voltage to the second current limiting device in response to a transient overvoltage on the second patient line, whereby the second current limiting device is switched off and limits current flow through the second patient line;
a second patient channel having first and second patient lines and having opposite first and second ends, the respective first ends being in communication with the internal circuit of the medical device, and the second ends comprising respective first and second patient interfaces, respective first and second current limiting devices in the first and second patient lines of the second patient channel;
a second biasing voltage generating circuit identical to the first mentioned biasing voltage generating circuit connected in a second line extending between the first and second patient lines of the second patient channel and configured for generating a bias voltage to turn off at least the respective first or second current limiting device of the second patient channel in the event of a transient voltage pulse in the first or second patient lines, respectively, of the second patient channel; and
at least one connecting line having a first end connected at a location between the first and second bias voltage generating circuits of the first patient channel and a second end connected at a location between the first and second bias voltage generating circuits of the second patient channel;
wherein the first and second biasing elements of the bias voltage generating circuits of the first and second patient channels comprise first and second biasing resistors and the at least one additional circuit element comprises a first resistor connected in series with the first biasing resistor and a second resistor connected in series with the second biasing resistor and the first resistor to form first and second voltage dividers, the junction between the resistors of the first voltage divider connected to the first current limiter device and the junction between the resistors of the second voltage divider connected to the second current limiter device, and the at least one connecting line has a first end connected between the first and second resistors of the first patient channel and a second end connected between the first and second resistors of the second patient channel.

17. A medical device comprising:
one or more electronic components;
at least one patient channel having first and second patient lines connecting electrical signals to or from the electronic components of the medical device, and first and second patient interfaces connected to the first and second patient lines, respectively; and an overvoltage protection circuit associated with the patient channel and comprising a first current limiter device located in the first patient line, a second current limiter device located in the second patient line, and first and second bias voltage generating devices located outside the first and second patient lines, respectively, and configured to generate a predetermined biasing voltage to turn off the respective first or second current limiting device to limit current flow through the first or second line, respectively, in response to a transient overvoltage on the first or second line, wherein first and second voltage generating devices comprise respective first and second biasing resistors each having a first end connected to the first and second patient line, respectively, and at least one voltage limiting device connected between the respective first and second biasing resistors to control the biasing voltage, and wherein said at least one voltage limiting device comprises a first resistor connected to the first biasing resistor to form a first voltage divider and a second resistor connected to the second biasing resistor in series with the first voltage divider and forming a second voltage divider.

18. The medical device of claim 17, wherein the first and second biasing resistors each have a resistance in the range of 10 kOhm to 1 MOhm and the first and second resistors each have a resistance in the range of 22 kOhm to 3.3 MOhm.

19. The medical device of claim 17, further comprising a first capacitor connected in parallel with the first resistor and a second capacitor connected in parallel with the second resistor.

20. The medical device of claim 19, wherein the first and second biasing resistors each have a resistance in the range of 10 kOhm to 1 MOhm and the first and second resistors each have a resistance in the range of 22 kOhm to 3.3 MOhm, and the first and second capacitors each have a capacitance in the range of 1 picofarad to 22 nanofarads.

* * * * *